US011400242B2

(12) United States Patent
Ziegler et al.

(10) Patent No.: US 11,400,242 B2
(45) Date of Patent: Aug. 2, 2022

(54) INHALER ADAPTED TO READ INFORMATION STORED IN DATA STORAGE MEANS OF A CONTAINER

(71) Applicant: Novartis AG, Basel (CH)

(72) Inventors: Dominik Ziegler, Basel (CH); Manfred Müller, Basel (CH); Richard Pavkov, East Hanover, NJ (US)

(73) Assignee: Novartis AG, Basel (CH)

( * ) Notice: Subject to any disclaimer, the term of this patent is extended or adjusted under 35 U.S.C. 154(b) by 447 days.

(21) Appl. No.: 15/741,630

(22) PCT Filed: Jun. 30, 2016

(86) PCT No.: PCT/EP2016/065349
§ 371 (c)(1),
(2) Date: Jan. 3, 2018

(87) PCT Pub. No.: WO2017/005605
PCT Pub. Date: Jan. 12, 2017

(65) Prior Publication Data
US 2018/0200460 A1    Jul. 19, 2018

(30) Foreign Application Priority Data
Jul. 3, 2015    (EP) .................... 15175216

(51) Int. Cl.
*A61M 15/00*    (2006.01)
*G16H 40/67*    (2018.01)

(52) U.S. Cl.
CPC .... *A61M 15/0035* (2014.02); *A61M 15/0065* (2013.01); *G16H 40/67* (2018.01);
(Continued)

(58) Field of Classification Search
None
See application file for complete search history.

(56) References Cited

U.S. PATENT DOCUMENTS 6,178,302 B1    1/2001    Nagashima et al.
6,958,691 B1 *  10/2005   Anderson ............ A61B 5/0002
                                                    340/539.12
(Continued)

FOREIGN PATENT DOCUMENTS

EP    3556414 A1 * 10/2019    ........ A61M 15/0065
JP    2009-001326 A    1/2009
(Continued)

OTHER PUBLICATIONS

Official action, dated Jan. 31, 2019, in RU appl. No. 2018103754/14.
(Continued)

*Primary Examiner* — Bradley H Philips
*Assistant Examiner* — Savannah L Gabriel
(74) *Attorney, Agent, or Firm* — Zollinger & Burleson Ltd.; Michael J. Mazza

(57) ABSTRACT

The present disclosure relates to an inhaler adapted to supply a formulation comprised in a container to a user, the inhaler being adapted to read information stored in data storage means of the container. The present disclosure also relates to a system comprising such an inhaler and the container comprising the formulation, the container further comprising the data storage means storing the information. The present disclosure also relates to a container comprising a formulation, the container further comprising data storage means storing information, the container being adapted for supplying the formulation to a user, wherein the container is adapted for usage in an inhaler of any of the preceding claims. The disclosure also relates to set comprising the inhaler and a computing device external of the inhaler, wherein the inhaler and the computing device are adapted to communicate with each other. The disclosure also relates to
(Continued)

the use of the inhaler, container, set and/or system for inhalation therapy.

18 Claims, 11 Drawing Sheets

(52) U.S. Cl.
CPC ....... *A61M 15/008* (2014.02); *A61M 15/0025* (2014.02); *A61M 15/0045* (2013.01); *A61M 15/0046* (2014.02); *A61M 2202/064* (2013.01); *A61M 2205/3306* (2013.01); *A61M 2205/3317* (2013.01); *A61M 2205/3561* (2013.01); *A61M 2205/582* (2013.01); *A61M 2205/6027* (2013.01); *A61M 2205/6054* (2013.01); *A61M 2205/6072* (2013.01); *A61M 2205/6081* (2013.01)

(56) References Cited

U.S. PATENT DOCUMENTS

| | | | |
|---|---|---|---|
| 7,151,456 B2* | 12/2006 | Godfrey | A61M 15/009 340/573.1 |
| 7,191,777 B2 | 3/2007 | Brand et al. | |
| 7,721,730 B2 | 5/2010 | Hamano et al. | |
| 8,251,914 B2 | 8/2012 | Daniels et al. | |
| 8,424,517 B2 | 4/2013 | Sutherland et al. | |
| 8,474,452 B2 | 7/2013 | Gumaste et al. | |
| 8,479,730 B2* | 7/2013 | Ziegler | A61M 15/0025 128/203.21 |
| 8,622,241 B2 | 1/2014 | Geboers et al. | |
| 8,807,131 B1 | 8/2014 | Tunnell et al. | |
| 8,985,113 B2 | 3/2015 | Aldana | |
| 9,016,147 B2 | 4/2015 | Adamo et al. | |
| 9,242,056 B2 | 1/2016 | Andersen et al. | |
| 9,390,457 B2* | 7/2016 | Baym | G09B 5/00 |
| 9,555,200 B2 | 1/2017 | Hosemann et al. | |
| 9,706,944 B2 | 7/2017 | Adamo et al. | |
| 9,744,319 B2 | 8/2017 | Denyer et al. | |
| 10,029,056 B2 | 7/2018 | Reilly et al. | |
| 10,258,753 B2 | 4/2019 | Adams et al. | |
| 10,463,816 B2 | 11/2019 | Calderon Oliveras et al. | |
| 10,682,476 B2 | 6/2020 | Curtis et al. | |
| 11,266,347 B2 | 3/2022 | Matthewson et al. | |
| 2002/0189615 A1* | 12/2002 | Henry | A61M 15/0048 128/203.21 |
| 2003/0074223 A1 | 4/2003 | Hickle et al. | |
| 2004/0025877 A1* | 2/2004 | Crowder | B65G 53/66 128/203.15 |
| 2005/0087473 A1* | 4/2005 | Fabricius | A61M 15/0045 206/534 |
| 2008/0110452 A1* | 5/2008 | Kotnik | A61M 11/00 128/200.14 |
| 2011/0298587 A1 | 12/2011 | Walz | |
| 2012/0003928 A1 | 1/2012 | Geboers et al. | |
| 2013/0146613 A1 | 6/2013 | Balthes | |
| 2013/0151162 A1 | 6/2013 | Harris et al. | |
| 2014/0053833 A1* | 2/2014 | Cline | A61M 15/008 128/203.12 |
| 2014/0182584 A1* | 7/2014 | Sutherland | A61M 15/0071 128/200.23 |
| 2015/0174349 A1* | 6/2015 | Tunnell | A61M 16/0051 128/200.14 |
| 2016/0081651 A1 | 3/2016 | Nam et al. | |
| 2016/0256639 A1* | 9/2016 | Van Sickle | G16H 20/13 |
| 2019/0030262 A1 | 1/2019 | Ziegler et al. | |
| 2022/0031973 A1 | 2/2022 | Matthewson et al. | |

FOREIGN PATENT DOCUMENTS

| | | |
|---|---|---|
| JP | 2011174788 A | 9/2011 |
| WO | 19920917231 A1 | 10/1992 |
| WO | 2003020349 A1 | 3/2003 |
| WO | 2013/016784 A1 | 2/2013 |

OTHER PUBLICATIONS

Search report, dated Jan. 29, 2019, in RU appl. No. 2018103754/14.
EPO Extended Search Report, dated Sep. 24, 2015, in EP appl. No. 15175216.9.
EPO examination report, dated Aug. 7, 2018, in EP appl. No. 15175216.9.
JPO official action, datd Mar. 3, 2019, in JP appl. No. 2017-567301.
EPO examination report, dated Apr. 3, 2020, in EP appl. No. 15175216.9.
EPO examination report, dated Sep. 7, 2020, in EP appl. No. 16741882.1.
Translation of JPO official action in JP appl. No. 2017-567301.
CNIPA examination report, dated Mar. 9, 2020, in CN appl. No. 201680046268.6.
Translation of JPO official action, dated Jun. 2, 2020, in JP appl. No. 2017-567301.
INPI examination report, dated May 12, 2020, in BR appl. BR112017028579-7.
CNIPA action in CN appl. No. 201680046268.6., dated Jan. 19, 2021.
EPO Communication under Rule 71(3) EPC, Intent to Grant, dated Apr. 9, 2021, EP appl. No. 15175216.9.
CNIPA action in CN appl. No. 201680046268.6, dated Jul. 7, 2021.

* cited by examiner

INHALER ADAPTED TO READ INFORMATION STORED IN DATA STORAGE MEANS OF A CONTAINER

CROSS-REFERENCE TO RELATED APPLICATIONS

This national stage entry application of international application PCT/EP2016/05349, filed 30 Jun. 2016, claims priority to European patent application no. 15175216.9, filed 3 Jul. 2015.

The present invention generally relates to an inhaler, a container comprising a formulation, a system comprising an inhaler and the container, a kit comprising the inhaler and a computing device, as well as the use of any of these devices for inhalation therapy.

It is known in the art that an inhaler may be used to supply a formulation comprised in a container to a user. For example, the container may be single-dose container, such as a capsule comprising the formulation, such as a medicament. However, alternatively, the container may also be a multi-dose container, such as a blister pack or strip comprising a plurality of blisters. Such a container may be placed in the inhaler. The user may then activate, e.g., pierce or open the container, such that the formulation may be released. The formulation may then be supplied to the user, e.g., by way of inhalation or also by way of an airflow generated by the inhaler.

While such containers, inhalers and systems comprising the container and the inhaler, as well as the usage of such devices for inhalation therapy, are known, they may have certain drawbacks and shortcomings.

It may, for example, be difficult for the user or a practitioner to monitor or control the correct usage of the devices. For example, the present devices may require the usage of a notebook to keep track of the status of the therapy. This may be particularly disadvantageous for elderly and forgetful users. Furthermore, if not keeping the correct track of the state of the therapy, an incorrect dosage may be provided to the patients—e.g., a wrong dosage may be provided to the patient, when two doses are administered on a single day, when the therapy requires only one dose to be administered per day.

The present invention is directed to overcome or at least alleviate the shortcomings and disadvantages associated with the prior art.

It is therefore an object of the present invention to provide above discussed devices and a respective use of the devices improving the monitoring and the control of inhalation therapy.

According to one aspect, the present invention relates to an inhaler adapted to supply a formulation comprised in a container to a user. The container comprises data storage means and the inhaler is adapted to read information stored in these data storage means.

For example, the information stored in the data storage means may include any of a batch number, an expiration date of the formulation and/or a container ID. This information can be read out by the inhaler. Thus, the inhaler "knows" which container is currently used to supply formulation to the user. This allows monitoring and control of the usage of the inhaler and the container. In other words, the formulation, which may be a pharmaceutical formulation, is trackable from its manufacture up to the point it is inserted into the inhaler and its inhalation.

Thus, it may be detected if and when the user inhales from the same container, such as a capsule, more than once and/or uses the same capsule again for inhalation therapy. Furthermore, it is possible to track and trace the complete path of the container from production down to the actual dose delivery, which may be advantageous for the manufacturer, e.g., for detection of counterfeiting. Furthermore, the same apparatus may be used to deliver multiple variants of formulations, such as drugs, and the apparatus may register the different variants. Furthermore, with such an apparatus, one can ensure that the user/patient does not use the same container (such as capsule) more than once; this is different to other devices not allowing for such a detection. Known tracking devices might instead provide a false positive result in case the same container is used more than once (i.e. indicating correct usage of the apparatus when it has been used repeatedly with the same container/compartment).

Correspondingly, the present invention also provides a respective container comprising a formulation. The container comprises data storage means storing information and the container is adapted for supplying the formulation to a user. For example, the container may be a single-dose container, such as a capsule, or a multi-dose container, such as a blister pack or strip.

In case the container is a multi-dose container, it may comprise a single data storage means or a plurality of data storage means. For example, the data storage means may be provided to an end portion to the container. Additionally or alternatively, the data storage means may be provided to or associated with different compartments of the multi-dose container.

The single-dose container typically comprises gelatin or HPMC (Hydroxypropyl Methylcellulose). The container may be filled, e.g., with a drum filler or dosing system, such as the ones obtainable by Harro Höfliger or MG2. The data storage means of the container may be realized in a variety of ways. For example, the data storage means may comprise a chip, which may be an RFID or a NFC component. Alternatively, the data storage means of the container may also comprise a transponder, a magnetic code, an electronic circuit chip or an optically readable bar code. Further alternatively or additionally, the data storage means of the container may also comprise a coloring detectable by light, such as a fluorescent dye.

The inhaler may comprise a corresponding unit to receive the respective information, e.g., an antenna, such as a low energy radio antenna, preferably an NFC antenna and/or RFID antenna. Alternatively or additionally, the inhaler may comprise an optoelectronic device to transmit and detect light, e.g., when the data storage means comprises a coloring detectable by light, such as a fluorescent dye.

The inhaler may comprise a detector to detect a magnetic field and/or an electric field, particularly also a change of these fields. Correspondingly, the container may be adapted to induce a magnetic field when moved to disrupt a magnetic and/or electric field to a detectable extend. This may allow the inhaler to detect a movement of the container, such as a spinning movement of the container. This will allow a more precise detection of airflow through the device.

Typically, a user places the single-dose container, such as a capsule, into the inhaler and then activates the container, e.g., by opening or piercing it.

In a passive inhaler, that is an inhaler which is operable solely by means of the user's inhalation, the user's inhalation results in the container moving within the inhaler. In other words, in passive inhalers, the formulation comprised in the container is released by means of the user inhaling. That is, e.g., in case the formulation is a powdered formulation, it is atomized by means of the user inhaling, such that the user may inhale the atomized formulation. That is, in passive inhalers, the air flow generated by the user inhaling is used for dispersion, e.g. by means of shear forces. In active inhalers, which are also envisaged by the present invention, the release (e.g. in case of a powdered formulation: the atomization) is achieved by additional means. The additional means may comprise a plate adapted to vibrate (e.g. by means of a piezo-element). Such a plate may, e.g., be positioned underneath the container comprising the formulation. The additional means may comprise a gas source comprising a gas, which is preferably stored in a compressed state, to atomize the formulation (such as in a pressurized metered-dose inhaler—also referred to as a puffer—which functions similar to a spray can; or in a nebulizer, which may comprise a compressor). In other words, in passive inhalers, additional means help to release the formulation (e.g. atomize the formulation in case of a powdered formulation) and air flow generated by the user's breath is used for inhalation of the atomized formulation.

Generally and particularly in passive inhalers, airflow generated by the user may force the container to spin or rotate within the inhaler. Such spinning or rotation may force or help the formulation stored in the container to exit the container. E.g., by means of the above described means, the inhaler may detect the amount of spinning or movement of the container. Thus, the inhaler may be able to determine whether the aerosolization is achieved to a satisfactory amount and how a patient has inhaled.

In one embodiment, the inhaler also comprises a transmitter to transmit information to another external device. Thus, information about the used container and the therapy, such as the speed of spinning and/or the quality of aerosolization, can be determined.

In one embodiment, the inhaler is adapted to detect whether the container has been opened or pierced. For example, the container, and in case the container is a multi-dose container, the individual compartments of the multi-dose container, may comprise an electrically conductive portion. Said electrically conductive portion may be pierced or opened by the inhaler for activation. Such piercing or opening of the electrically conductive portion may change an electric characteristic of the container, which can be measured by the inhaler. Thus, the inhaler may determine whether the container or the individual compartment has been opened or pierced. Thus, it can also be determined whether the container or compartment to be used has been opened correctly. That may ensure that the capsule is actually pierced when inhaling—which is different to other known devices which would provide false positive results in a case where an unpierced container is used.

In one embodiment, the inhaler is adapted to assume an unlocked state and a locked state, the unlocked state allowing the formulation to be supplied to the user and the locked state not allowing the formulation to be supplied to a user. Such locked and unlocked states may be realized by a variety of ways. Advantageously, such an inhaler also comprises data receiving means. Such data receiving means are adapted to receive data. Furthermore, the inhaler may be adapted to change from one state to another that is from the locked state to the unlocked state and/or vice versa, in the response to data received by the data receiving means. Thus, the inhaler may be remotely controlled to change from one state to another. For example, a practitioner may unlock the inhaler. Furthermore, the unlocking could also be provided by a respective timing—e.g., the unlocking could always occur at a certain time during the day when the formulation is to be supplied to a user. This further facilitates correct usage of the inhaler.

According to another aspect, the present invention also relates to a set comprising any of the inhalers discussed herein and an external computing device, the inhaler and the computing device being adapted to communicate with each other. For example, the external computing device can be a smartphone. In such a set, it may be possible that the user can activate (e.g. switch from a locked state to an unlocked state) the inhaler by means of the computing device; e.g. by entering a PIN into the computing device or simply by means of the computing device being in a communication range of the inhaler. This may, for example, ensure that the inhaler only be used by the correct user.

The present invention is also defined by the following numbered aspects:

1. An inhaler adapted to supply a formulation comprised in a container to a user, the inhaler being adapted to read information stored in data storage means of the container.
2. An inhaler according to the preceding aspect, wherein the inhaler is a passive inhaler, i.e. an inhaler operable solely by means of the user's inhalation.
3. An inhaler according to any of the preceding aspects, wherein the inhaler comprises a body and a chamber for receiving the container, at least one air inlet connected to the chamber via an air passage and a mouthpiece including an outlet and an inhalation passage adapted to connect to the chamber.
4. An inhaler according to the preceding aspect, wherein the mouthpiece is pivotally mounted to an edge of the body such that it is pivotable between an open loading position and a closed dispensing position about an axis that is perpendicular to a longitudinal axis of the inhaler.
5. An inhaler according to the preceding aspect, the body including a pair of opposed axle slots that accommodate hinge axles that project from a hinge member of the mouthpiece, a back of the body further including a groove to help the user distinguish the back of the device from the front.
6. An inhaler according to any of the 3 preceding aspects, wherein the at least one air passage is tangentially disposed to the chamber.
7. An inhaler according to any of the 4 preceding aspects, wherein the chamber is formed to allow the container to spin within the chamber about a longitudinal axis of the inhaler.
8. An inhaler according to any of the 5 preceding aspects, wherein the body comprises two or more interlocking body portions that secure the mouthpiece to the edge of the body.
9. An inhaler according to any of the 6 preceding aspects that includes a removable cap and mouthpiece guides are provided on the inner surface of the cap that engage the mouthpiece.
10. An inhaler according to the preceding aspect, wherein ribs are provided on the inner surface of the cap adjacent the mouth of the cap that engage the body of the inhaler.
11. An inhaler according to any of the 8 preceding aspects that contains a capsule that contains a powdered medicament.
12. An inhaler according to the preceding aspect, wherein the medicament is suitable for the treatment of asthma, chronic obstructive pulmonary disease or cystic fibrosis by pulmonary inhalation.
13. An inhaler according to any of the 10 preceding aspects, wherein the body includes a portion which is substantially cylindrical in shape with a diameter longer than the container to be contained therein and a height greater than the diameter of the container, but less than the length of the container and an airflow path defined between the at least one air inlet and the outlet is arranged to make the container spin within the chamber.
14. An inhaler according to any of the preceding aspects, wherein the inhaler comprises an antenna.
15. An inhaler according to the preceding aspect, wherein the antenna is a low power radio antenna, such as an NFC antenna and/or an RFID antenna.
16. An inhaler according to any of the preceding aspects, wherein the inhaler comprises an optoelectronic device to transmit and detect light.
17. An inhaler according to any of the preceding aspects, wherein the inhaler comprises a magnetic field detector and/or an electric field detector.
18. An inhaler according to the preceding aspect, wherein the detector is adapted to detect the change of a magnetic and/or electric field.
19. An inhaler according to any of the preceding aspects, wherein the inhaler is adapted to detect a movement, such as a spinning movement, of the container.
20. An inhaler according to any of the preceding aspects, wherein the inhaler comprises a transmitter to transmit information to another device.
21. An inhaler according to the preceding aspect, wherein the transmitter is a wireless transmitter.
22. An inhaler according to any of the two preceding aspects, wherein the transmitter is a Bluetooth, Bluetooth low energy (BLE), ZIGBEE, Z-WAVE, infrared (IR), WLAN such as WIFI, RF, near-field communication (NFC), or an optical transmitter.
23. An inhaler according to any of the preceding aspects, wherein the inhaler comprises activation means to activate the container.
24. An inhaler according to the preceding aspect, wherein the activation means is an opening means to open the container.
25. An inhaler according to the preceding aspect, wherein the opening means is a piercing means, such as a piercing means comprising a needle or a sharpened pin.
26. An inhaler according to the preceding aspect, wherein the piercing means comprise at least one and preferably two spring biased push-button(s) that each include at least one piercing element.
27. An inhaler according to any of the three preceding aspects, wherein the inhaler is adapted to detect whether the container or a target compartment of the container is opened or pierced.
28. An inhaler according to the preceding aspect, wherein the container comprises an electrically conductive portion, for example a coating, and wherein the inhaler is adapted to measure an electric characteristic of the container, the electric characteristic to be measured by the inhaler being dependent on whether the container or the respective compartment of the container is opened or pierced.
29. An inhaler according to the preceding aspect, wherein the electric characteristic is at least one of current, voltage and resistance.
30. An inhaler according to any of the preceding aspects, wherein the inhaler is adapted to assume an unlocked state and a locked state, the unlocked state allowing the formulation to be supplied to the user and the locked state not allowing the formulation to be supplied to a user.
31. An inhaler according to the preceding aspect, wherein the unlocked state allows placement of the container into the inhaler and the locked state does not allow such placement.
32. An inhaler according to any of the two preceding aspects, wherein the unlocked state allows opening and closing of the inhaler and the locked state does not allow such opening and closing.
33. An inhaler according any of the three preceding aspects, wherein the unlocked state allows activation of the container, such as opening or piercing the container, and the locked state does not allow such activation.
34. An inhaler according to any of the four preceding aspect, wherein the inhaler comprises data receiving means adapted to receive data, the inhaler being adapted to change from one state to another in response to data received by the data receiving means.
35. An inhaler according to the preceding aspect, wherein the data receiving means are wireless data receiving means.
36. An inhaler according to the preceding aspect, wherein the data receiving means include at least one of Bluetooth, Bluetooth low energy (BLE), ZIGBEE, Z-WAVE, infrared (IR), WLAN such as WIFI, RF, near-field communication (NFC), and optical data receiving means.
37. An inhaler according to any of the preceding aspects, wherein the inhaler is a single-dose inhaler.
38. An inhaler according to any of the aspects 1 to 2 or 14 to 36, when not dependent on any of the aspects 3 to 13, wherein the inhaler is a multi-dose inhaler for supplying formulation comprised in a multi-dose container comprising a plurality of compartments.
39. An inhaler according to the preceding aspect, wherein the inhaler comprises an advancing mechanism, the advancing mechanism being adapted for advancing the container by a predetermined distance each time the advancing mechanism is engaged.
40. An inhaler according to any of the two preceding aspect, wherein the inhaler comprises a housing, a withdrawing assembly disposed at least partially within the housing, the withdrawing assembly being adapted for facilitating withdrawal of formulation from a target compartment of the container and conveying the formulation toward an exterior of the inhaler device.
41. An inhaler according to the preceding aspect, wherein the withdrawing assembly comprises a piercing member adapted for opening the target compartment while the target compartment is positioned in the withdrawing assembly.
42. An inhaler according to any of the two preceding aspects, wherein the inhaler comprises a compartment track disposed within the housing, the compartment track being adapted for guiding each compartment of the container to the withdrawing assembly in succession and storing the container prior to, during, and after use of the compartment of the container.
43. A system comprising
an inhaler according to any of the preceding aspects,
the container comprising the formulation, the container further comprising the data storage means storing the information.
44. A container comprising a formulation, the container further comprising data storage means storing information, the container being adapted for supplying the formulation to a user.

45. A container according to the preceding aspect, wherein the container is adapted for usage in any of the inhalers of the preceding aspects.
46. A container according to any of the two preceding aspects, wherein the container comprises an electrically conductive portion.
47. A container according to the preceding aspect, wherein the electrically conductive portion is a coating.
48. A container according to any of the four preceding aspects, wherein the container is a single-dose container.
49. A container according to any of the aspects 44 to 47, wherein the container is a multi-dose container.
50. A container according to the preceding aspect, wherein the container comprises a plurality of separated compartments comprising the formulation.
51. A container according to the preceding aspect, wherein at least one of the compartments comprises data storage means.
52. A container according to any of the two preceding aspects, wherein a plurality of the compartments, and preferably all, comprise data storage means, respectively.
53. A container according to any of the 4 preceding aspects, wherein an end portion of the container comprises data storage means.
54. A container according to any of the 4 with the features of aspect 50, wherein the compartments each include an electrically conductive portion.
55. An inhaler, container and/or system according to any of the preceding aspects, the container being adapted to induce a magnetic field when spinning.
56. An inhaler, container and/or system according to any of the preceding aspects, wherein the container is adapted to disrupt a magnetic and/or electric field to a detectable extent.
57. An inhaler, container and/or system according to any of the two preceding aspects, wherein the data storage means contributes to or provides the container with the magnetic-field-inductive or field-disruptive property.
58. An inhaler, container and/or system according to any of the preceding aspects, wherein the data storage means is a passive data storage means.
59. An inhaler, container and/or system according to any of the preceding aspects, wherein the data storage means is an active data storage means.
60. An inhaler, container and/or system according to any of the preceding aspects, wherein the data storage means comprises at least one of a transponder, magnetic code, an electronic circuit chip and an optically readable bar code.
61. An inhaler, container and/or system according to any of the preceding aspects, wherein the data storage means comprises an RFID component, such as a chip.
62. An inhaler, container and/or system according to any of the preceding aspects, wherein the data storage means comprises an NFC component, such as a chip.
63. An inhaler, container and/or system according to any of the preceding aspects, wherein the data storage means comprises a coloring detectable by light, such as a fluorescent dye.
64. An inhaler, container and/or system according to any of the preceding aspects, wherein the information stored in the data storage means includes any of a batch number, an expiration data and/or a container ID.
65. An inhaler, container and/or system according to any of the preceding aspects, wherein the container is a capsule.
66. An inhaler, container and/or system according to the preceding aspect, wherein the capsule contains the formulation.
67. An inhaler, container and/or system according to the preceding aspect, wherein the formulation is a powder.
68. An inhaler, container and/or system according to any of the preceding aspects, wherein the inhaler is adapted to receive the container.
69. An inhaler, container and/or system according to any of the preceding aspects, wherein the formulation is a pharmaceutical formulation.
70. A set comprising
    an inhaler according to any of the preceding aspects preferably with the features of aspect 20 and/or 34 and
    a computing device external of the inhaler;
    wherein the inhaler and the computing device are adapted to communicate with each other.
71. A set according to the preceding aspect,
    wherein the computing device comprises data output means adapted to output data.
72. A set according to the preceding aspect,
    wherein the data output means comprises a display adapted to display the data.
73. A set according to any of the two preceding aspect,
    wherein the inhaler is adapted to transmit information stored in the data storage means of the container to the computing device; and
    the computing device is adapted to at least partially output this information on the data output means.
74. A set according to any of the 4 preceding aspects,
    wherein the inhaler comprises the features of aspect 30,
    wherein the inhaler is adapted to change from one state to another in response to data received by the computing device.
75. A set according to any of the 5 preceding aspects,
    wherein the inhaler is in the locked state when it is not in communication with the computing device.
76. A set according to any of the 6 preceding aspects,
    wherein the computing device is selected from a group consisting of: a personal computer, a smart phone, a smart watch, a wearable device, a tablet computer, and a laptop computer.
77. A set according to any of the 7 preceding aspects,
    wherein the computing device is configured to:
    attempt to connect with the inhaler in response to the user providing a trigger;
    pair with the inhaler with a medical device application; and
    send one or more messages to the inhaler indicating parameters for operation of the inhaler.
78. A set according to any of the 8 preceding aspects,
    wherein the inhaler is configured to:
    send a message to a medical device application on the computing device in response to a triggering event;
    pair with the medical device application on the computing device; and
    send one or more messages to the medical device application indicating status and/or parameters for operation of the inhaler.
79. A set according to the preceding aspects, wherein the triggering event is selected from a group consisting of: the user depressing a button on the inhaler, the inhaler being brought within a wireless communication range of the computing device, and an attempt to utilize the inhaler.
80. The use of the inhaler, container, system and/or set of any one of the preceding claims for inhalation therapy.

The present invention will become more fully understood from the detailed description given herein after and the accompanying drawings which are given by way of illustration only, and thus, are not limiting of the present invention.

Figure 1:
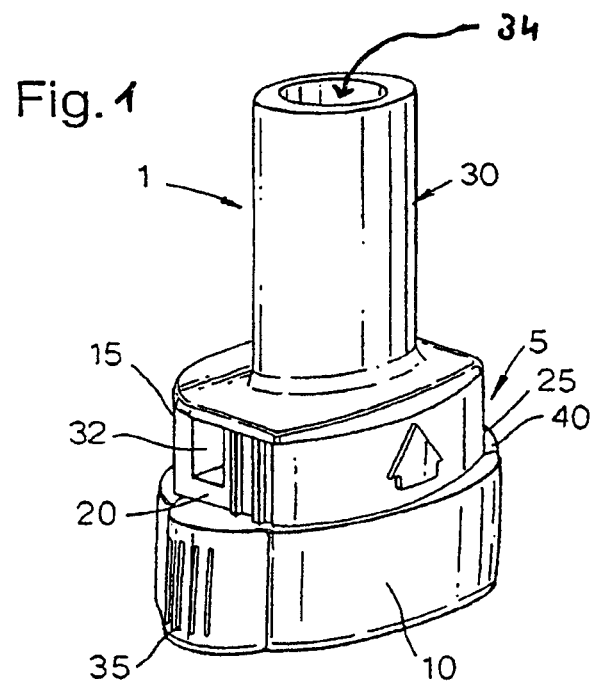
FIG. 1 shows a plan view of a first embodiment of the present invention in a first configuration.

FIG. 1 depicts an inhaler 1 (also referred to as inhalation device, medical device or simply device). As shown in FIG. 1, inhaler 1 has a body 5 that has a front 10, a back 15, a first side 20 and a second side 25. The body 5 is formed from two interlocking body portions. The device 1 has a mouthpiece 30 that is pivotally attached to the back 15 of the body 5 and can be moved between an open position and a closed position. The mouthpiece includes an outlet 34. In FIG. 1 the mouthpiece 30 is in its closed position. The device also has at least one, and preferably a pair of air inlets 32. A pair of push-buttons 35 and 40 protrudes from the sides 20 and 25 of the body 5, whose function is explained below.

Figure 2:
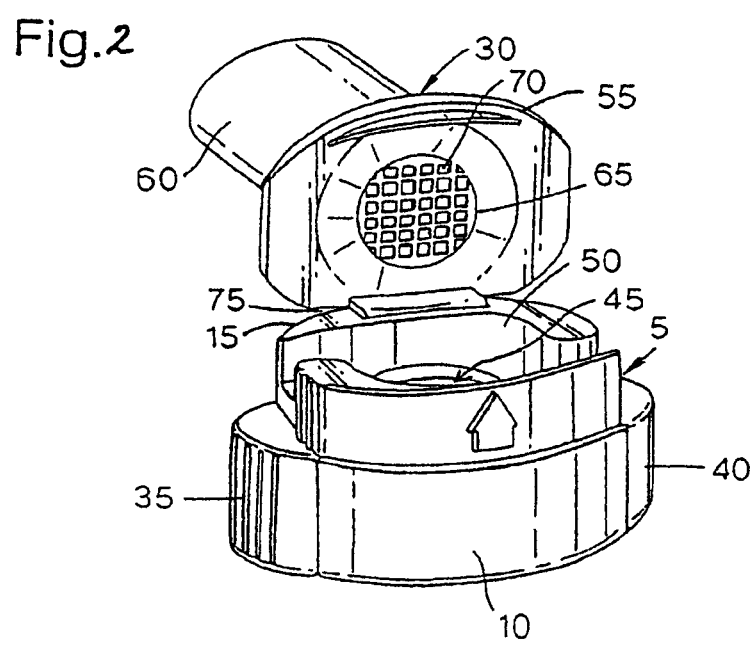
FIG. 2 shows a plan view of the embodiment depicted in FIG. 1 in a second configuration.

FIG. 2 shows the preferred embodiment of the inhaler 1 with the mouthpiece 30 in its open position. When the mouthpiece is in its open position the user can load a container, such as a capsule (not shown in this Figure) containing a formulation, such as a medicament into a chamber 45, also referred to as capsule chamber 45, that is formed within a recess 50 in the body 5. The recess 50 has a circular cross-section for a purpose that is described below.

The mouthpiece 30 comprises a flange 55 and a tube 60. The flange 55 has a perforated plate or grid 65 that provides access to a coaxially disposed inhalation passage 70 that is formed within the tube 60.

The tube 60 of the mouthpiece can be any practical length however it is generally desirable to keep its length to a minimum as this reduces the area upon which powder can deposit and accumulate on the inhalation passage 70. This also helps to minimize the need for cleaning the device 1. The tube 60 is preferably substantially cylindrical and the cross-section of the inhalation passage 70 formed therein is preferably substantially round or substantially ellipsoidal so that in use the air that is swirling in the recess and carrying the medicament continues to swirl as it passes through the inhalation passage 70 and into the user's mouth.

The mouthpiece is pivotally attached to the back 15 of the body 5 by a hinge member 75. The hinge is formed to allow the mouthpiece to be moveable between its open position and its closed position about an axis that is perpendicular to the longitudinal axis of the inhaler 1. By hinging the mouthpiece to the body of the inhaler in that way the user can simply and conveniently open the device to load it with a capsule by gripping the body 5 with one hand, for example by placing a thumb on the front 10 of the body 5 and a forefinger on the back 15 of the body 5, and then pushing the tube 60 of the mouthpiece 30 backwards using the other hand, or perhaps the chin or even some stationary object such as a shelf or table. This construction avoids many of the real difficulties that some users experience when trying to open other inhalers. This is especially true for users who are old, fragile, disabled or for some other reason have impaired dexterity that makes it difficult or perhaps even impossible for them to grip certain inhalers or to use inhalers that require a swivel or some other twisting action to be opened.

The hinge is preferably formed to permit the mouthpiece to be pivoted without the need to apply an excessive torque but also to avoid or at least substantially minimize any gaps between the flange 55 of the mouthpiece 30 and the body 5 when the mouthpiece is in its closed position. The hinge provides a secure attachment so that the mouthpiece is not readily detachable from the body. This may be achieved by trapping the hinge within the two interlocking body portions (not shown). This is particularly important when users lack fine motor skills in their hands. It also serves to prevent the mouthpiece being lost.

Figure 3:
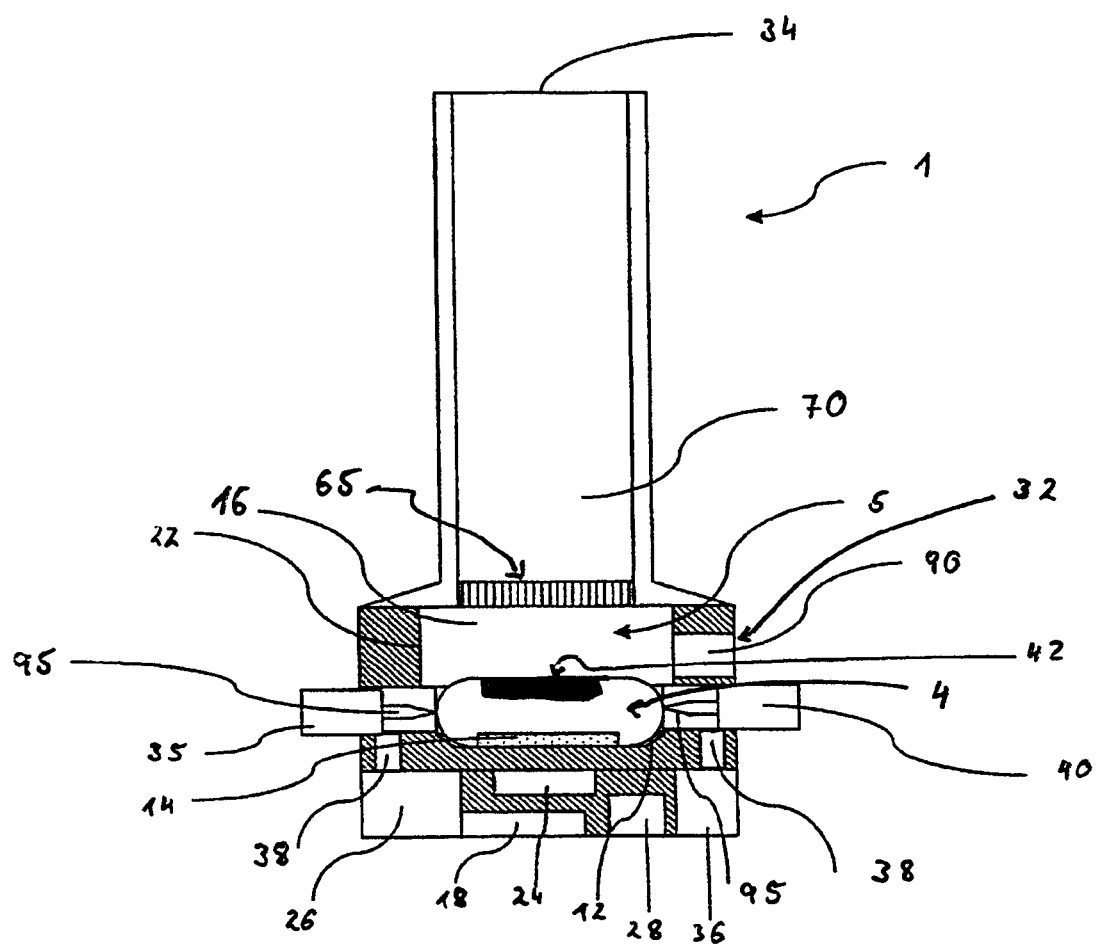
FIG. 3 shows a cross sectional view of the embodiment in FIG. 1.

FIG. 3 shows a cross sectional view through an inhaler 1. The inhaler 1 may comprise any of the features discussed in conjunction with FIGS. 1 and 2 and 5 to 7. The inhaler 1 comprises a body, housing or capsule housing 5 containing a container, such as medicament capsule 4. The inhaler 1 comprises an airflow path comprising the inhalation passage 70 through which air flows during an airflow event, which may be triggered by a user inhaling. The airflow path extends from at least one air inlet 32 to an outlet 34 and passes through the capsule housing 5. The at least one inlet 32 enters the capsule housing 5 away from a centreline. In this example a top part 16 of the capsule housing 5 is substantially cylindrical and the air enters substantially tangentially by at least one tangential air passage 90 to the capsule housing 5 to encourage the air to swirl within the capsule housing 5. The top part 16 of the capsule housing 5 is substantially cylindrical in shape with a diameter longer than a capsule 4 contained therein and a height greater than the diameter of the capsule 4, but less than the length of the capsule 4. The capsule housing 5 includes a bottom part 12, or coffin, in which the capsule 4 initially rests. The container or capsule 4 comprises (here: contains) a formulation 14, such as a dry powder medicament formulation.

As depicted, the container, that is in this embodiment the capsule 4, may include data storage means 42. The data storage means 42 may be an active or a passive data storage means. Examples of the data storage means 42 include a transponder, a magnetic code, an electronic circuit chip and an optically readable bar code. The data storage means 42 may comprise an RFID or an NFC component, for example. The data storage means 42 may also comprise a coloring detectable by light, such as a fluorescent dye. The data storage means 42 may be printed, coated or otherwise applied to capsule 4. They may be positioned both on the outside or on an inside portion of capsule 4. The data storage means 42 stores information about the capsule 4, such as formulation contained therein, date of the expiry, batch number, container ID, etc.

The inhaler 1 may be adapted to read the information stored in the data storage means 42 of the capsule 4. In the present embodiment, the inhaler 1 may comprise an information receiving unit 24. This unit is adapted to receive the information stored in the data storage means 42. For example, where the data storage means 42 of the container 4 is an RFID component, the information receiving unit 24 may comprise an RFID antenna. Conversely, e.g., if the data storage means 42 of the capsule 4 is an NFC component, the information receiving unit 24 may include an NFC antenna. And if the data storage means 42 comprise a coloring detectable by light, the information receiving unit 24 may include an optoelectronic device adapted to transmit and detect light. Furthermore, the inhaler 1 may also comprise a processor unit 18 adapted to interpret the information received by information receiving unit 24. However, the processor unit 18 could alternatively also be present within an external device. In any case, processor unit 18, together with information receiving unit 24, is adapted to read the information stored in data storage means 42.

In the preferred embodiment, which is depicted, the inhaler 1 also comprises a power source 26, which may, for example, be a battery or a rechargeable battery. The power source 26 may provide electric energy to the respective electrical components. In the depicted embodiment, the inhaler 1 also comprises a transmitter 36. Transmitter 36 may be adapted to transmit information to an external device by any communication protocol.

The depicted inhaler 1 also comprises external data receiving means 28 adapted to receive data or information from an external device. Again, this may be done by any communication protocol.

As previously discussed, the inhaler 1 may assume an open position, as depicted in FIG. 2, and a closed position as depicted in FIG. 1. As will be understood, the inhaler 1 can only be used as intended, when the user may switch between the open position and the closed position—the open position is needed to place a capsule 4 into the inhaler 1 and the closed position is needed to inhale through the inhaler 1. The state where the user may switch between the open and closed position at will may therefore be referred to as an active or functional state. Conversely, a state where the mouthpiece 30 is locked in either the open or the closed position may be referred to as a passive or non-functioning state. That is, in other words, in the active or functional state, the inhaler 1 may be used as intended and in the passive and non-functioning state, normal usage of the device 1 is prohibited. Preferably, the inhaler 1 is adapted to assume both the active or functional state, which may also be referred to as the unlocked state, and the inactive and non-functioning state, which may also be referred to as the locked state. For example, the locked state may be a state where the inhaler 1 is locked in either the open or the closed state. This may, for example, be achieved by a locking mechanism (not shown) locking either the hinge member 75 or a closing member (not shown) locking the mouthpiece 30 in the closed position. The locking and/or closing member may be activated in response to data or information received by the data receiving means 28. Thus, a remote control of the inhaler 1 may be achieved. For example, the inhaler 1 may normally assume the locked or inactive state and only assume its unlocked or active state, when activated, e.g., by a timing corresponding to the timing prescribed by a healthcare professional or by unlocking by a remote device.

In above paragraph, the locked and unlocked state have been described in conjunction with the inhaler 1 being changeable from its open to its closed state or being not changeable between these positions. However, it will be readily apparent that this is not the only possibility for the inhaler 1 to assume unlocked or locked positions. As described above, the inhaler comprises at least one piercing member 95 associated with a respective actuator or push button 35, 40. The inhaler 1 may also assume its active or passive, i.e. its unlocked and locked position or configuration by unlocking and locking the respective button 40 with the associated piercing member 95. This may be achieved by respective locking members 38 (i.e. one locking member 38 for each piercing member 95 and button 35, 40). The locking members 38 may lock the button 35, 40 and the piercing member 95 in a locked position, not allowing usage of these members. Thus, in the locked state, it is not possible to pierce or activate the container 4. Again, it is preferred that the locking members 38 may be adapted to change their positions in response to a respective external signal received by the data receiving means 28. Again, this may allow the usage of the inhaler 1 to be controlled remotely, e.g. by a respective program or by a healthcare professional.

Alternatively or additionally, the inhaler 1 may also be adapted to assume its locked and/or its unlocked state in response to a signal generated by the processor 18. For example, the processor 18 may interpret the data received by the information receiving unit 24 and being indicative of the data stored in the data storage means 42 of the capsule 4 and only activate the inhaler 1, that is bring the inhaler 1 into its unlocked state, when a certain condition (e.g., right capsule 4 and right timing) is met.

In a preferred embodiment, the container 4 containing or comprising the formulation 14 includes a portion, which is electrically conductive. For example, this section may be a section of the surface and preferably the complete surface or one or both longitudinal end sections of the surface. The inhaler 1 may be adapted to measure an electric characteristic of the container 4. The electric characteristic may, for example, be the electric resistance, current flowing through a section of the capsule 4 and/or the voltage across a section of the capsule 4. This characteristic may change depending on whether or not the capsule 4 has been pierced. This allows the inhaler 1 to determine whether or not the capsule 4 placed in the inhaler 1 has been pierced.

It is further preferred that the container 4, e.g., by virtue of its electrically conductive portion and/or by virtue of its data storage means, may induce a magnetic field and/or may disrupt a magnetic and/or an electric field sufficiently for this disruption to be detected. By this characteristic, a movement, in particular a spinning of the container 4, may be detected by the inhaler 1. To do so, the inhaler 1 may also include a unit to measure a magnetic and/or electric field, and particular the changes of any one of these fields.

The capsule housing 5 is defined by at least one wall 22 and is configured such that when a capsule 4 is located in the capsule housing 5 and sufficient air flows along the airflow path 6, the capsule 4 is drawn into the top part 16 of the capsule housing 5 and spins in the airflow.

The inhaler 1 also includes a pair of actuator or push buttons 35, 40 which are coupled to piercing members 95, such as needles or pins. The buttons 35, 40 can be pressed by a user to cause the piercing members 95 to pierce holes in the ends of a capsule 4 arranged in the bottom part 12 of the capsule housing 5.

To use the device correctly a user is required to load a capsule into the inhaler, press the buttons to pierce the capsule and then inhale through the device such that the capsule is agitated and spins in the airflow such that a powder medicament therein is dispensed from the capsule and entrained in the airflow to the patient.

Figure 4:
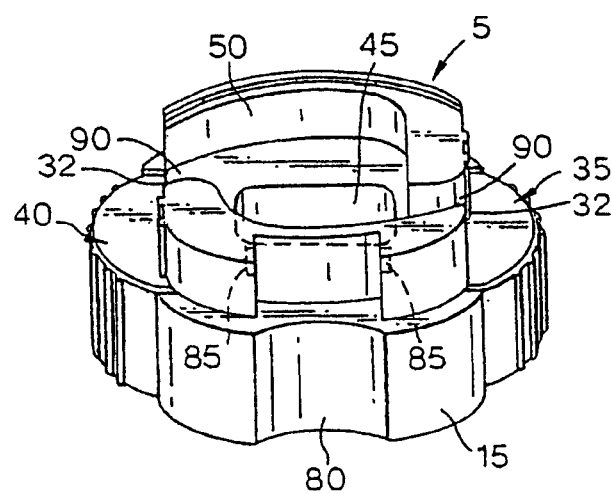
FIGS. 4 and 5 show details of the embodiment depicted in FIG. 1.

The internal construction of the body 5 is seen in FIG. 4. This is a back perspective view showing the capsule chamber 45 with the recess 50. The back 15 of the body 5 has a groove 80 that helps the user to distinguish the back of the device from the front of the device. The body has a pair of opposed axle slots 85 that accommodates hinge axles (not shown) that project from the hinge member 75 of the mouthpiece 30.

The pair of air passages 90 may in this embodiment be formed between the body 5 and the flange 55 of the mouthpiece 30 (when in its closed dispensing position) that communicate between the air holes or air inlets 32 on the external surface of the device and the recess 50 within the device. These air passages 90 are tangentially disposed to the recess 50 for a purpose that is described above and will also be described below.

In use the user moves the mouthpiece 30 from its closed position (seen in FIG. 1) to its open position (seen in FIG. 2) as described above and places a capsule (not shown) containing a powdered medicament to be administered in the capsule chamber 45 of the recess 50. Suitable indicia may be provided on the device to indicate to the user how the mouthpiece can be moved to its open position and where the capsule should be placed. The user then moves the mouthpiece back to its closed position ready for dispensing the medicament. The user presses both push-buttons 35 and 40 substantially simultaneously to activate a capsule piercing mechanism. This mechanism is illustrated in FIGS. 3 and 5.

Figure 5:
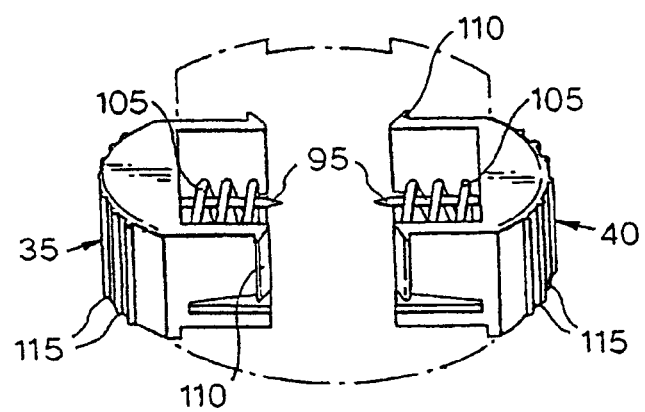

As seen in FIG. 5, the capsule piercing mechanisms comprises a pair of piercing members, such as needles or sharpened pins 95 that project inwardly from the push-buttons 35 and 40. The tips are preferably shaped like hypodermic needles and may be beveled (i.e. sliced at an angle) or symmetrically pointed to pierce the capsule cleanly and with minimal resistance. The opposed orientation of the needles serves to restrict the movement of the capsule in the capsule chamber during the piercing action and thus ensures a clean and effective perforation. The shape of the tips can also assist in restricting the movement of the capsule in the capsule chamber. For example when the tips of the pins are beveled such that the beveled surface faces the floor of the capsule chamber 45, the capsule will tend to be pushed towards the floor of the capsule chamber 45 as the pins penetrate the capsule. Each push-button 35/40 is transversely slidable within a gallery (not shown). In each case the push-button is urged outwards by a spring 105 that is constrained against a bush (not shown). The spring ensures the pins 95 retract from the perforated capsule when the user is no longer applying pressure to the push-buttons 35 and 40. Each push-button has a pair of shoulders 110 that abuts an inner wall of respective gallery to prevent the push-button being able to slide out of the gallery completely. Gripping elements 115 are provided on the push-buttons to assist the user to retain a good grip on the push-buttons while pushing them together to pierce the capsule.

Once the capsule has been pierced by the needles 95 the medicament contained therein is available to be administered by pulmonary inhalation. The user should release the push-buttons to allow the needles 95 to retract from the pierced capsule and then grip the body of the device once again, for example by once again placing a thumb on the front 10 of the body and a forefinger on the back 15 of the body. Users administer the medicament by breathing out fully, inserting the mouthpiece 30 into the mouth, sealing placing their lips and teeth around the mouthpiece and inhaling quickly and deeply. This action draws surrounding air into the device through the air inlets 32, along the air passages 90, and into the recess 50. The air passages 90 are positioned substantially tangentially with respect to the recess 50 so this rush of air into the recess 50 forms a vortex in the recess 50. This vortex in the recess lifts the perforated capsule out from the capsule chamber 45 and causes the capsule to spin rapidly about the longitudinal axis of the inhaler. The recess 50 has a substantially circular cross-section to accommodate the spinning capsule. The length of the capsule is slightly less than the diameter of the recess 50 so there are repeated impacts between the ends of the capsule and the side wall of the recess 50, which causes the powdered medicament from within the capsule to be drawn out through the perforations in the ends of the capsule, this being assisted by the spinning motion of the capsule itself. The powdered medicament is entrained with the air passing through the perforated plate 65 and along the inhalation passage 70 of the mouthpiece 30. The walls that define the airflow path and these passages, recesses and tube are formed with smooth curves to minimize air resistance and thereby minimize the effort that is required of the user to inhale the medicament. The perforated plate or grid 65 prevents the capsule being inhaled up the tube 60.

If necessary this inhalation action is repeated. When the capsule has been spent, which is more easily seen with the capsule casing being transparent, the user moves the mouthpiece from its closed (dispensing) position to its open (loading) position and discards the spent capsule. The device is then ready to be reloaded with a fresh capsule containing the desired medicament and reused.

Figure 6:
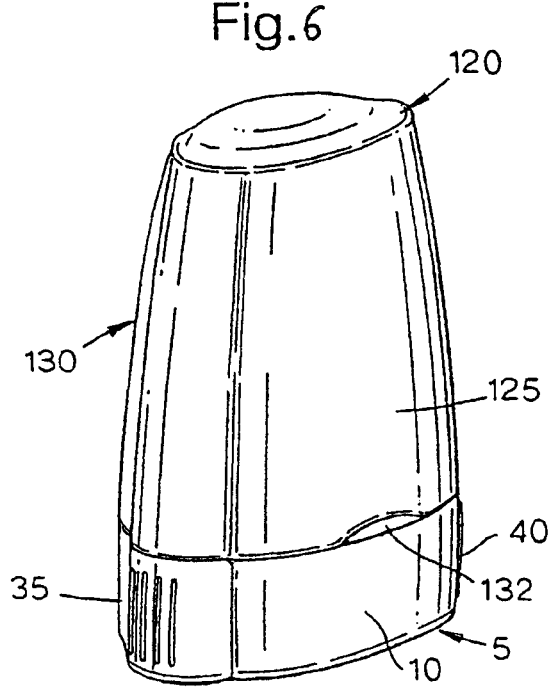
FIG. 6 shows a plan view of another configuration of the embodiment depicted in FIG. 1.

The preferred embodiment of the device has a removable cap 120, which has a front 125 and a back 130. This is shown in FIGS. 5 and 6.

As seen in FIG. 5, the cap 120 is formed to snap fit to the body 5 and completely cover the mouthpiece 30 and upper part of the body 5. A finger access recess 132 is formed by providing indentations in the lower edge of the front 125 of the cap 120 and, if desired, the front 10 on the body 5. This gives the user a visual and tactile cue to pull the cap 120 from the body 5 by gripping the body in one hand and inserting a finger, most conveniently a thumb, of the other hand into the finger access recess 132 and gently prying the cap 120 away from the body 5.

Figure 7:
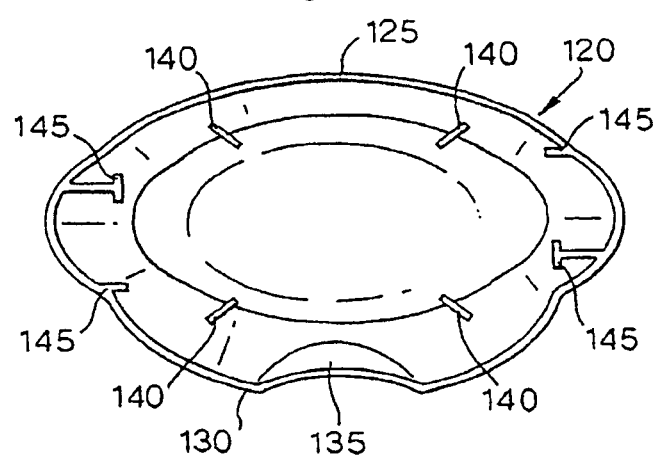
FIG. 7 shows further details of the embodiment of FIG. 1.

As seen in FIG. 7, which is an underneath plan view of the cap 120, the back 130 of the cap 120 includes a grooved area 135 that helps the user to distinguish the back of the device from the front of the device and encourage the user to orient the device in the manner that is most convenient to use it. This is especially important when that user is visually impaired. The grooved area 135 of the cap 120 is contoured to meet and complement the groove 80 of the body 5.

If desired, a set of mouthpiece guides 140 is provided on the inner surface of the cap 120 that engages the tube 60 of the mouthpiece 30 when the cap 120 is placed over the mouthpiece 30 and the body 5 of the device. If desired, a set of ribs 145 is provided on the inner surface of the cap 120 adjacent its mouth that engages the body 5 of the inhaler when the cap 120 is placed on the device. The mouthpiece guides 140 and the ribs 145 serve to stiffen the cap and help to prevent the cap being unintentionally separated from the body, for example during storage or transportation. This is important as many people who use inhalers carry them with them wherever they go, often in some sort of bag together with a variety of other things. The cap is provided with smooth contours with this in mind.

Hitherto, the description of the drawings was particularly directed to embodiments, where a single-dose container or capsule 4 could be placed in the inhaler 1, that is a container 4 containing a single-dose of the formulation to be supplied to a user. However, the present invention is not limited to such single-dose inhalers. Instead, the present invention can also be applied to inhalers for usage with containers for multiple usage. Such an embodiment of the present invention will now be described with reference to FIGS. 8A to 8C.

In this embodiment, the formulation is comprised in a multi-dose container 202, such as a blister strip 202. Such a multi-dose container 202 comprises a plurality of compartments 210 (also referred to as blisters in the present embodiment), wherein the compartments 210 comprises the formulation or formulations to be supplied to the user. In this embodiment, the multi-dose container 202 comprises data storage means 42.

The multi-dose container 202, in the depicted embodiment, includes a leading edge 208 or leading end 208 and a trailing end or trailing edge 209. The leading edge 208 is the portion close to the formulation to be supplied first to the user and the trailing edge 209 is the portion close to the formulation to be supplied last to the user.

Figure 8A:
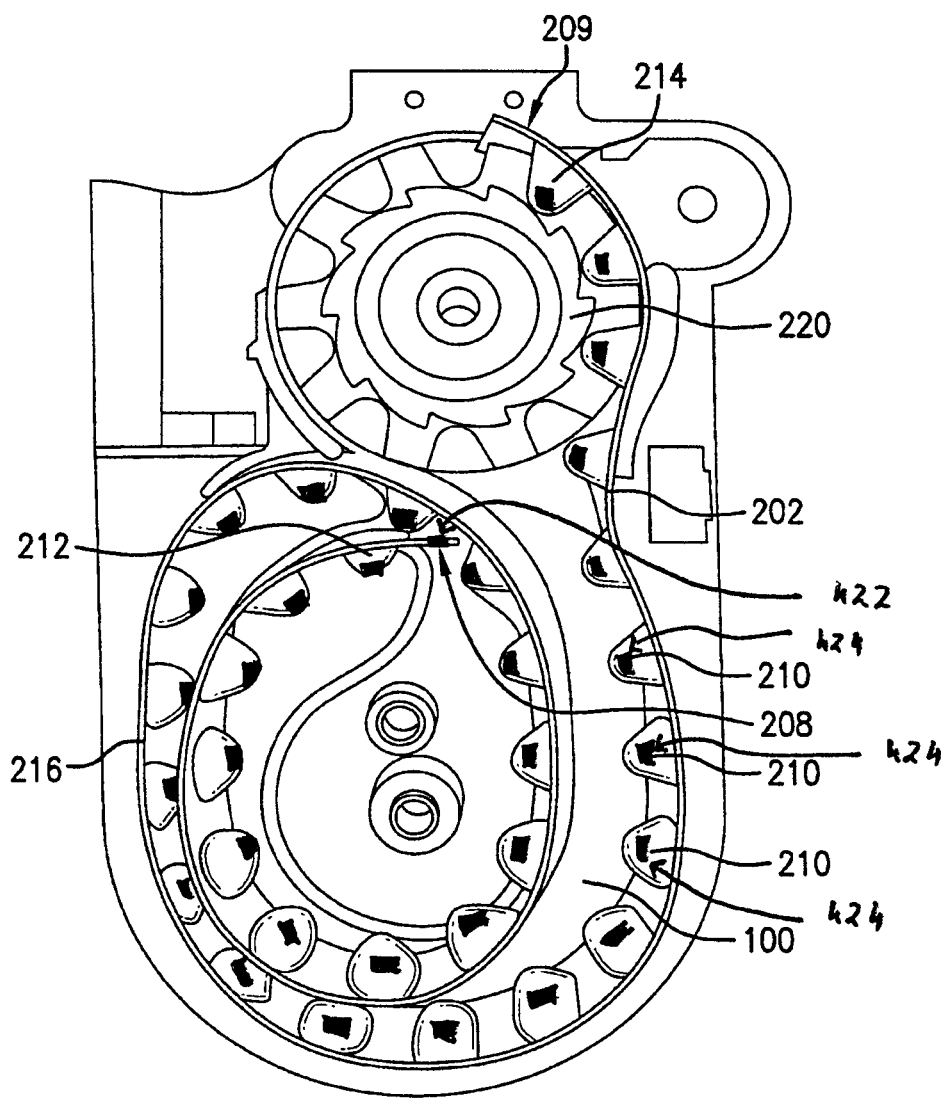
FIGS. 8A and 8B show further embodiments of the present invention.

In the present multi-dose container embodiment, the data storage means 42 may be embodied in a variety of ways. For example, the data storage means 42 may comprise a leading edge data storage means 422 located at or near the leading edge 208 of the multi-dose container 202. Alternatively or additionally, individual compartments or blisters 210 may include compartment data storage means 424. In FIG. 8A, all the compartments 210 are depicted to comprise such a compartment data storage means 424 (although, for sake of simplicity, only three of them are provided with the respective numeral). However, as depicted, e.g., in FIG. 8B, it is also possible to provide only some (such as only half) of the compartments with such compartment data storage means 424. Each of the described data storage means 42 may be embodied as described above.

Figure 8B:
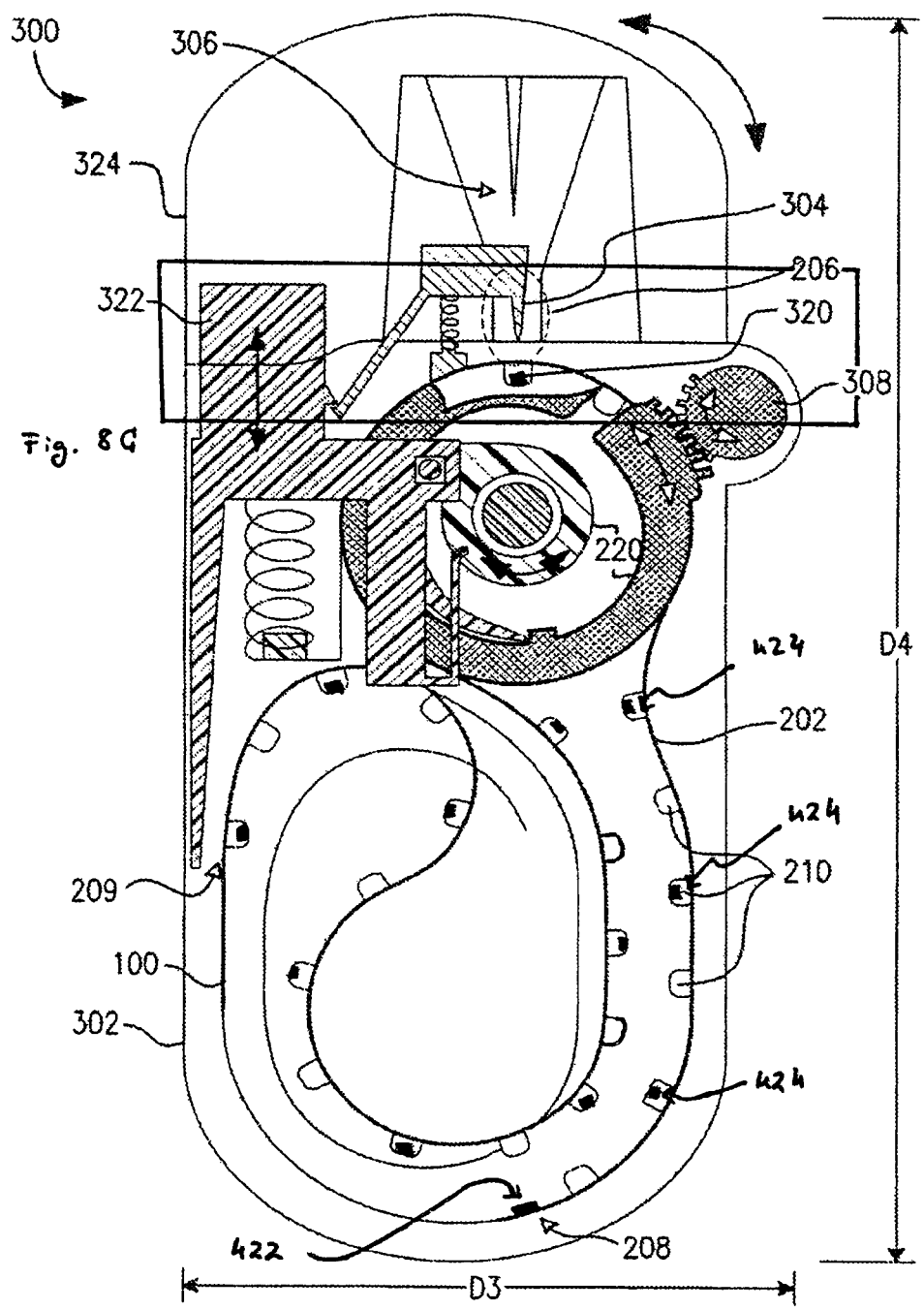
Figure 8G:
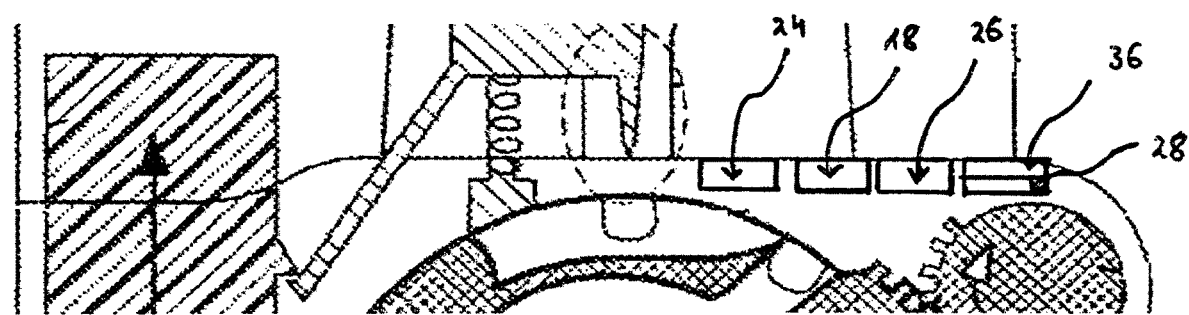
FIG. 8C shows a detail of the embodiment depicted in FIG. 8B.

For simplicity of illustration, the details of the depicted inhalers allowing the information stored in the data storage means to be read out are not depicted in FIGS. 8A and 8B, but only in the enlarged FIG. 8C. As described above, the inhaler may comprise an information receiving unit 24 to receive the information or data stored by the data storage means 42, a processor 18 adapted to interpreted the information or data received by the information receiving unit 24, as well as a power source 26, such as a battery unit. Furthermore, if desired and as discussed above, the inhaler may also comprise a data receiving means 28 to receive data from an external device and/or a transmitter 36 to transmit information to an external device, for corresponding reasons as above. All these structures may be realized as discussed above. Furthermore, the above discussed locking mechanisms may also be provided to the embodiment discussed in conjunction with FIGS. 8A to 8C and the compartments of the multi-dose container may be provided with electrically conductive portions, allowing the inhaler to detect whether a target compartment has been opened.

Further constructional details of the embodiment depicted in FIGS. 8A to 8C will now be described. Additional constructional details of this embodiment are disclosed by US 2015/0090262 A1. Such constructional details are incorporated herein by reference.

Referring to FIG. 8A, an image of an inhaler device with a separate end path loaded with a multi-dose container or blister strip 202 in a final position is shown, according to one embodiment. As can be seen from this image, the leading edge 208 of the blister strip 202 may contact or come close to contacting the blister strip 202 at a point near an intersection. FIG. 8B shows an engaging element and details of an withdrawing assembly, according to one embodiment.

FIG. 8A also shows a portion of an advancing mechanism 220, according to one embodiment.

In some embodiments, a first blister 212 in the blister strip 202 may contain formulation, such as a medicament, in which case the blister strip 202 may have a plurality of blisters 210, such as 31 blisters 210, one for each day of a 31-day month. In months that include less than 31 days, the inhaler device may be disposed of with blisters 210 remaining in a position prior to the withdrawing assembly 206 and/or unopened. When the first blister 212 does not contain medicament, there may be 32 blisters 210 present on the blister strip 202 to account for each day of a 31-day month, plus the blank first blister 212. It may be particularly advantageous to use an empty first blister 212 to verify expected operation of the inhaler device. For example, an empty first blister 212 may be utilized to test performance of the opening element, the dispensing element, the engaging element, and/or the advancing mechanism 220, along with positioning of the blister strip 202 within the inhaler device, in various approaches.

FIG. 8B shows a simplified schematic diagram of an inhaler device 300, according to one embodiment. As shown, the inhaler device 300 comprises a housing 302, a withdrawing assembly 206 disposed at least partially within the housing 302, the withdrawing assembly 206 being adapted for facilitating withdrawal of medicament from a target blister 320 of a blister strip 202 and conveying the medicament toward an exterior of the inhaler device 300. The withdrawing assembly 206 comprises an opening element 304 adapted for opening the target blister 320 of the blister strip 202 while the target blister 320 is positioned in the withdrawing assembly 206. The opening element 304 may also be referred to as a piercing member or a pin needle. The opening element 304 is operable by a user. The withdrawing assembly 206 also comprises a dispensing element 306 adapted for directing the withdrawn medicament toward the exterior of the inhaler device 300.

Furthermore, the inhaler device 300 also comprises a blister track 100 disposed within the housing 302, the blister track 100 being adapted for guiding each blister 210 of the blister strip 202 to the withdrawing assembly 206 in succession and storing the blister strip 202 prior to, during, and after use of blisters 210 of the blister strip 202. The blister track 100 may comprise coil structures, according to one embodiment. In addition, the blister track 100 may comprise a low or very low friction material, such as polycarbonate (PC), acrylonitrile butadiene styrene (ABS), polybutylene terephthalate (PBT), polyoxymethylene (POM) also referred to as acetal plastic, and other polymers as would be understood by one of skill in the art, in various embodiments. Of course, the blister track 100 may comprise other materials in combination with or without the plastic or polymer, such as metals, resins, and/or other suitable materials.

The inhaler device 300 also comprises the advancing mechanism 220 disposed within the housing 302, the advancing mechanism 220 being adapted for advancing the blister strip 202 by a predetermined distance each time the advancing mechanism 220 is engaged, and an engaging element 308 adapted for engaging the advancing mechanism 220 to advance the blister strip 202, the engaging element 308 being operable by the user.

For example, as can be seen in FIG. 8B, the inhaler device 300 includes the housing 302. The housing 302 may comprise a plastic or polymer material, such as polycarbonate (PC), acrylonitrile butadiene styrene (ABS), polybutylene terephthalate (PBT), polyoxymethylene (POM) also referred to as acetal plastic, and other polymers as would be understood by one of skill in the art, in various embodiments. In particular, the housing 302 may comprise a material having a low or very low coefficient of friction. Of course, the housing 302 may comprise other materials in combination with or without the plastic or polymer, such as metals, resins, and other suitable materials. In FIG. 8B, the housing 302 appears only behind the components of the inhaler device 300 in order to illustrate the other components of the inhaler device 300, but in operation the housing 302 may include all the components of the inhaler device 300, in order to provide rigidity and protection to the inhaler device 300, among other functions. In some embodiments, the housing 302 may include only some of the components, while other components may be external of the housing 302, such as all or a portion of the dispensing element 306, in some approaches.

In some embodiments, the blister strip 202 may be discontinuous (e.g., not a loop, having a starting and ending portion) and may have a consistent pitch between centers of adjacent blisters 210, e.g., the distance between each blister 210 on the blister strip 202 is the same. In some embodiments, the consistent pitch between centers of adjacent blisters of the blister strip 202 may be less than about 12 mm, such as less than 11 mm, or less than 10 mm or less than 9 mm or less than 8 mm. Some pitch, is however, important, and may depend upon characteristics of the material used in the blister strip. Thus in some embodiments a pitch is between 5 and 10 mm, such as between 6 and 9 mm. In some embodiments, the pitch may be about 8 and 9 mm. In some embodiments, the blister strip 202 may comprise 32 blisters 210 comprising 31 blisters 210 having a medicament therein prior to withdrawal therefrom, and a first blister 212 having no medicament therein.

In some embodiments and as shown in FIGS. 8A and 8B, the advancing mechanism 220 may be a wheel structure with a plurality of grooves or notches defined by a plurality of teeth. Each tooth may be configured to accept a blister 210 of the blister strip 202. In operation, the blisters 210 arranged along the blister strip 202 fit into the grooves or notches. Furthermore, the advancing mechanism 220 drives the blister strip 202 along the blister track 100 by rotating in a clockwise direction (according to the perspective shown in FIG. 8B), thereby pushing the leading edge 208 of the blister strip 202 while pulling the trailing edge 209 of the blister strip 202 and requiring a relatively low amount of torque in order to operate. In some embodiments, the advancing mechanism 220 may comprise a track wheel positioned at a predetermined distance from the blister track 100 and adapted for advancing the blister strip 202 along the first radius of the primary coil structure, such as by a distance (in some embodiments equal to the pitch) between centers of adjacent blisters.

According to some embodiments, the inhaler device 300 may optionally include a counter mechanism (not shown) adapted for displaying a number of blisters 210 in the blister strip 202 which have been opened or have not been opened, e.g., the number of blisters 210 in the blister strip 202 remaining, or alternatively, the number of blisters 210 in the blister strip 202 that have been opened/used.

In some embodiments, the housing 302 may comprise two pieces of a structure coupled together, such as a clamshell configuration, molded plastic pieces, a top and bottom piece, etc., as would be understood by one of skill in the art upon reading the present descriptions. As shown in FIG. 8B, the housing 302 appears as a structure cut away above the shaded portion.

Referring again to FIG. 8B, in operation, the opening element 304 breaches one or more surfaces of the target blister 320 and establishes a connection between the target blister 320 and the dispensing element 306 via the withdrawing portion 206 of the inhaler device 300. Formulation/medicament contained within the target blister 320 may be conveyed from the target blister 320 toward the dispensing element 306 and subsequently toward the exterior of the inhaler device 300. In one particular embodiment, the opening element 304 may include a hollow piercing element adapted for piercing the target blister 320 and allowing withdrawal of medicament from the target blister 320 through the piercing element toward the dispensing element 306 and an operating element 322 adapted for causing the piercing element to engage the target blister 320 upon operation of the operating element 322.

In some embodiments, the dispensing element 306 may include one or more fluid configuration components, devices, elements or means to assist in enabling the patient's inspiratory efforts to evacuate and/or aerosolize the medicament withdrawn from the target blister 320. Such components, devices, elements or means act to direct, shape, alter, or enhance air flow and/or air pressure. In some embodiments, the fluid configuration components or means act to direct airflow at an angle to the blister surface of between about 0 and 90 degrees. In some embodiments the fluid configuration components or means may comprise a Venturi tube. In some embodiments the fluid configuration components or means may comprise one or more vanes. In some embodiments, the dispensing element 306 may comprise a mouthpiece adapted for conveying the withdrawn medicament of the target blister 320 toward the user. Any mouthpiece may be used as known in the art, and the mouthpiece may be replaceable, removable, permanent, rigid, pliable, cleanable, etc., as would be understood by one of skill in the art. Moreover, the mouthpiece may include a plurality of outlets therein sufficient to direct the withdrawn medicament of the target blister 320 to the user upon inhalation by the user. In one such embodiment, two outlets may be provided within the mouthpiece.

In operation, a user interacts with the inhaler device 300 to receive a delivery of medicament. For example, in one embodiment, the user may operate the opening element 304 of the withdrawing assembly 206, which opens the target blister 320 positioned in the withdrawing assembly 206 and permits medicament to flow from the target blister 320 to the dispensing element 306 within the withdrawing assembly 206 and subsequently to the user. After receiving medicament, the user operates the engaging element 308, which may comprise a moveable cap 324 adapted for covering the mouthpiece in one embodiment. Upon user operation, the engaging element 308 engages the advancing mechanism 220 in order to advance the blister strip 202 by a predetermined distance each time the advancing mechanism 220 is engaged. Subsequent doses of medicament may be accessed by repeating this process until all medicament has been dispensed from the inhaler device 300, e.g., the blister strip 202 has been moved from initial position to final position.

The moveable cap 324 and housing 302 as shown in FIG. 8B are transparent in order to visualize the components contained therein and/or behind. Of course, in practice the inhaler device 300 may utilize a moveable cap 324 and/or housing 302 of any degree of transparency or opacity. In various embodiments, the moveable cap 324 and the opening element 304 may be interlocked such that the moveable cap 324 engages the advancing mechanism 220 when the moveable cap 324 is transitioned from an open position to a closed position only after the opening element 304 has been operated. That is to say, the engaging element 308 only engages and operates the advancing mechanism 220 after medicament has been dispersed from the inhaler device 300 and/or the target blister 320 has been opened by the opening element 304.

According to some embodiments, the inhaler device 300 may have overall dimensions of less than about 12.0 cm by about 7.5 cm by about 3.5 cm. For example, as shown in FIG. 8B, a width D3 of the inhaler device 300 may be less than about 7.5 cm, such as about 5.5 cm, in one approach. Furthermore, a length D4 of the inhaler device 300 may be less than about 12.0 cm, such as about 11.5 cm, in one approach. Although not shown in FIG. 8B, a depth (into the page) of the inhaler device 300 may be less than about 3.5 cm, such as about 3.0 cm in one approach.

The inhaler device of the present invention can be made of any suitable material, for example a tough plastics material such as acrylonitrile-butadiene-styrene (ABS), methyl-methacrylate-acrylonitrile-butadiene-styrene (MABS) or an anti-static material. If desired, the material is substantially transparent to help the user to more readily see and understand how the device works. This encourages users to use the device in the correct way and continue to use the device in that manner for the full term of their treatment, i.e. increase compliance.

The container for use in the inhaler device of the present invention contains a powdered medicament that is suitable for inhalation. The medicament is preferably suitable for the treatment of asthma or chronic obstructive pulmonary disease, for example one or more bronchodilators, anti-inflammatories or combinations thereof. Preferred bronchodilators include beta-2 adrenoceptor agonists such as albuterol (salbutamol), salmeterol, formoterol, and pharmaceutically acceptable salts thereof, and compounds (in free or salt or solvate form) of formula I of WO 00/75114 or WO 04/16601, and antimuscarinic agents such as ipratropium bromide, oxitropium bromide, tiotropium, glycopyrrolate, and pharmaceutically acceptable salts thereof, and compounds (in salt or zwitterionic form) of formula I of WO 04/96800 or WO 05/00815. Preferred anti-inflammatory drugs include steroids, in particular glucocorticosteroids such as budesonide, beclamethasone dipropionate, fluticasone propionate, ciclesonide or mometasone furoate, or steroids described in WO 02/00679.

The foregoing description describes an inhaler adapted to supply a formulation comprised in a container to a user and a preferred embodiment thereof. In practicing the invention, it is to be understood that the use and construction of the various parts can be modified to meet specific requirements.

Figure 9:
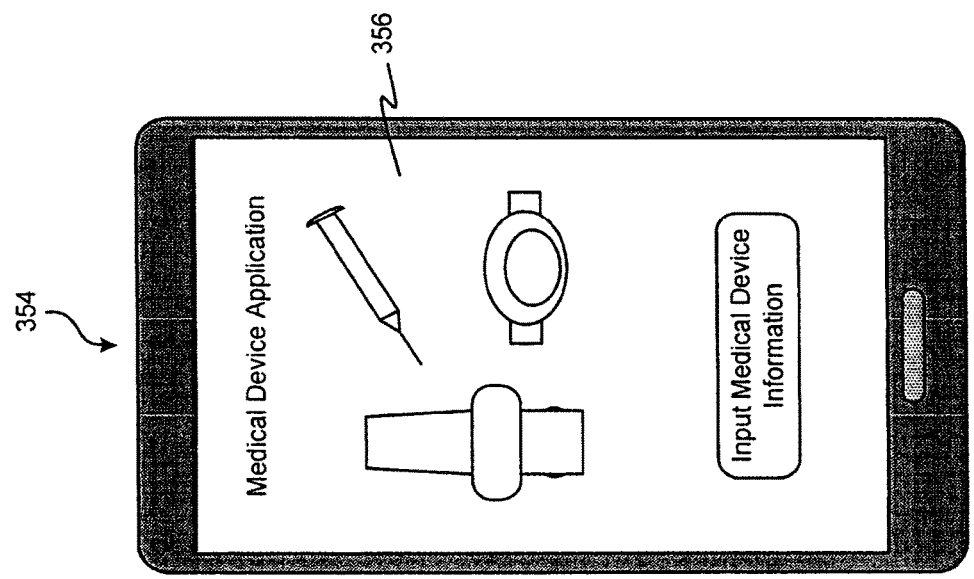
FIG. 9 shows a medical device in the form of an inhaler and a computing device, according to one embodiment.
Figure 9:
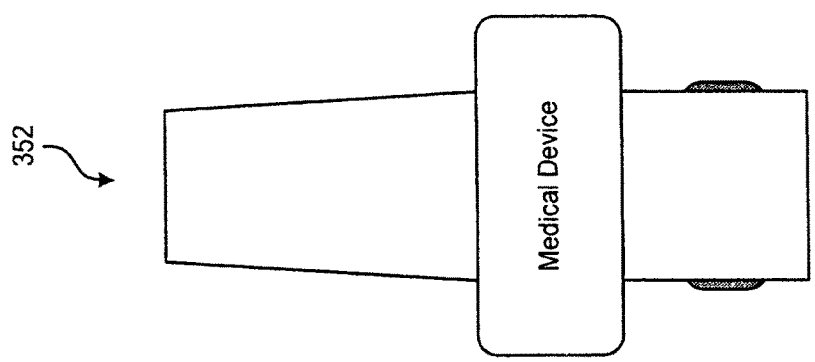

Now referring to FIG. 9, a medical device 352 is shown along with a computing device 354, according to one embodiment. In this embodiment, the invention also relates to a set comprising the medical device 352 (e.g. the inhaler) and the computing device. In the discussed embodiment, the medical device 352 is an inhaler, such as any of the inhalers discussed herein. That is, the inhaler 352 may comprise any of the features discussed herein. In this embodiment, the computing device 354 may comprise any computing device known in the art, such as a personal computer (PC), a mobile telephone (e.g., a smart phone (such as APPLE iPHONE, SAMSUNG GALAXY S3, S4, S5, etc.), cell phone, etc.), a tablet computer (such as an APPLE iPAD, MICROSOFT SURFACE, SAMSUNG GALAXY TAB, AMAZON KINDLE, etc.), a smart watch (e.g., MOTOROLA MOTO360, ASUS ZENWATCH, APPLE iWATCH, etc.), a laptop computer, an ultrabook computer, or a wearable device (e.g., head-up displays including GOOGLE GLASS and others, tracking and displaying devices like FITBIT).

The computing device 352 is capable of communicating via one or more wireless communication technologies. Any wireless communication technology capable of receiving a signal and transmitting data to/from the medical device 352 may be used, as would be known to one of skill in the art upon reading the present descriptions.

In one embodiment, the computing device 354 is a smart phone, as shown, capable of downloading program applications from a central application server. Any central application server may be used to download program applications, such as APPLE APP STORE, APPLE iTUNES, GOOGLE PLAY STORE, AMAZON APP STORE, etc. Any of these application servers may include a medical device application 356 (here: inhaler device application) that may be downloaded onto the computing device 354. Medical device applications may also be downloadable from servers under the control of the provider of the medical device, healthcare providers, pharmacies, hospitals, clinicians, or doctors.

In some embodiments, the medical device 352 may be any medical device known in the art capable of communicating with the computing device 354 via a wireless communication technology, such as any of the discussed inhalers having external data receiving and/or transmitting means 28, 36. Any wireless communication technology may be used for transmitting the signal from the medical device 352 to the medical device application 356, as would be known to one of skill in the art upon reading the present descriptions.

Some exemplary wireless communication technologies include, but are not limited to, Bluetooth, Bluetooth low energy (BLE), ZIGBEE, Z-WAVE, infrared (IR), WLAN such as WIFI, RF, near-field communication (NFC), and optical.

In another embodiment, a proprietary wireless communication protocol may be used to send information between the medical device 352 and the computing device 354, with the proprietary communication protocol being configured to effectively convey information specific to the medical device 352 and uses thereof.

In some examples, the medical device 352 may communicate via NFC, a Bluetooth-capable implantable insulin injector, etc. In one embodiment, the medical device 352 is an inhaler configured to communicate via BLE and/or Bluetooth.

In some further embodiments, the medical device 352 (i.e. the inhaler) may comprise a processor capable of executing logic, a local memory for storing data, and logic which may be accessible to the processor and/or implemented within the processor. The logic may be configured to cause the medical device to follow instructions from the computing device, send information from the medical device 352 to the computing device 354, a networked storage device, other devices within a network, and/or a cloud, and receive information from the computing device 354, a networked storage device, other devices within a network, and/or a cloud.

The local memory of the medical device 352 may comprise any memory known to one of skill in the art, such as RAM, ROM, non-volatile memory (NVM) such as Flash memory, removable memory such as a microSD card.

In accordance with one embodiment, a user of the computing device 354 may install a medical device application 356 on the computing device 354. The medical device application 356 may be downloaded from an application server accessible to the computing device 354, the application server being of a type known in the art. In another embodiment, the medical device application 356 may be provided to the computing device 354, for example via a computer readable storage medium, such as a CD, MicroSD card, RAM, or ROM, and/or virtually provided via a link and/or pointer that is embedded in a communication received by the computing device 354, such as a hypertext link in an email, or HTML pointer in a text message. The computing device 354 may then access the medical device application 356 via the Internet, a WLAN such as a WIFI network, a WAN, a LAN, etc., to install the medical device application 356 on the computing device 354, as would be understood by one of skill in the art upon reading the present descriptions.

Figure 10:
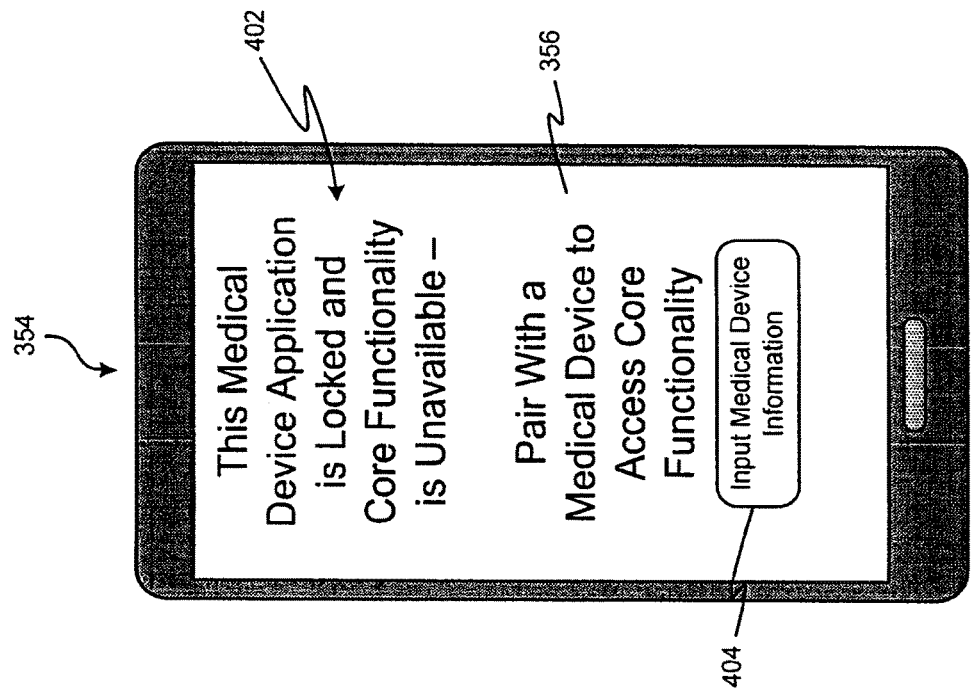
FIG. 10 shows a medical device application in a locked state, according to one embodiment.
Figure 10:
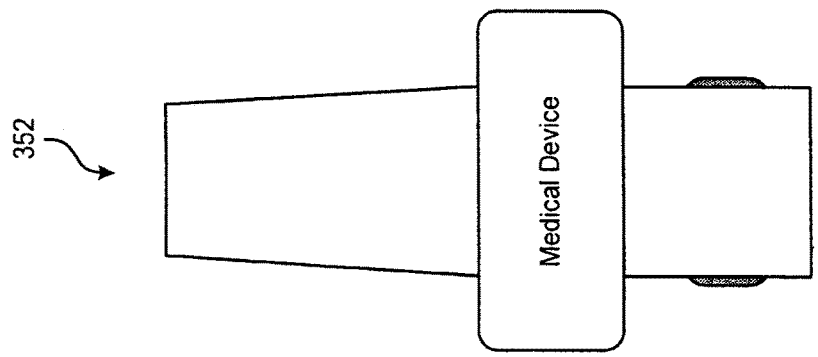

After the user has caused the medical device application 356 to become installed on the computing device 354 and started, executed, run, and/or opened the medical device application 356 on the computing device 354, the medical device application 356 will indicate that it will not provide complete functionality until it has been shifted from a locked state to an unlocked state, as shown in FIG. 10, in accordance with one embodiment. The medical device 352, e.g. the inhaler, may assume the locked and unlocked states in any of the ways discussed herein.

In an alternate embodiment, the medical device application 356 may be unlocked upon installation, and will allow the user to access all functionality thereof. However, a medical device 352 may not function unless it has been unlocked by the medical device application 356.

The screen displayed in FIG. 10 is an embodiment of a message 402 describing that the medical device application 356 requires that the medical device 352 be paired with the medical device application 356 in order for the medical device application 356 to provide some of the medical device application 356 functionality. As shown, link 404 provides access to a second screen (not shown) which may provide some functionality, for example, the ability to input user information and medical device 352 information so that once the medical device 352 is paired with the medical device application 356, the medical device application 356 is ready to provide full functionality consistent with and operable by the particular medical device 352.

In another embodiment, pairing the medical device 352 to the medical device application 356 may be accomplished by simply confirming, such as by touching a button on a display screen of the computing device, that a medical device recognized by the medical device application 356 and indicated on a display of the medical device application 356 is the medical device 352 in possession of the user. The indication of the medical device 352 may comprise a unique code, some programmed name recognizable by the user, a default name of the medical device, a symbol representing the medical device, or some other indication known in the art.

In some embodiments, a medical device 352 is provided which has multiple use modes, and the medical device application 356 may similarly provide multiple use modes which correspond to the particular use modes of the medical device 352. In this embodiment, the medical device 352 is configured to unlock only the functionality of the medical device application 356 which is appropriate to the desired use mode of the medical device 352. For example, the medical device 352 may be an inhaler which may be suitable to deliver different drugs, or different classes of drugs.

By "pairing," what is meant in one embodiment is that the medical device 352 and the medical device application 356 have connected to one another, with the medical device application 356 recognizing the medical device 352, and the medical device 352 providing at least some information to the medical device application 356.

Some functions may still be accessible by the user while the medical device application 356 is in the locked state, such as altering settings, inputting personal information, inputting information about the medical device 352, etc., in various approaches. However, core functionality of the medical device application 356 may only be accessed while the medical device application 356 is in the unlocked state (as discussed in detail above). Core functionality may include functions that enable a medical device 352 to operate, functions that allow collection of data from a medical device 352, and functions that allow the medical device application to communicate to the medical device 352.

Furthermore, in one embodiment, only functionality of the medical device application 356 that is appropriate for a particular medical device 352 may become accessible in the unlocked state, such as to prevent confusion with the operation of the medical device application 356 and/or to simplify a user interface of the medical device application 356 (such as when operating more than one type of medical device with the medical device application 356). By appropriate, what is meant in one embodiment is that the functionality is consistent with and intended for the medical device 352.

In some embodiments, a user may possess two medical devices 352 such as smart inhalers, each smart inhaler being configured to provide one or more of a different medicament, dose, formulation, or compound. For example, one smart inhaler may provide a drug for treatment of chronic obstructive pulmonary disease (COPD) while the other smart inhaler may provide a drug for the treatment of asthma. In such embodiment(s), the medical device application 356 may therefore recognize and understand the differences between the medical devices (smart inhalers) and may only provide functionality on the medical device application 356 for the particular smart inhaler that is currently paired to the medical device application 356. In this way, particular operating parameters of the different smart inhalers together with patient posology will be accounted for and provided in the medical device application 356, for example dosage amount, frequency of dosage, drug interactions, and adverse effect warnings, when a particular smart inhaler is currently paired to the medical device application 356.

Figure 11A:
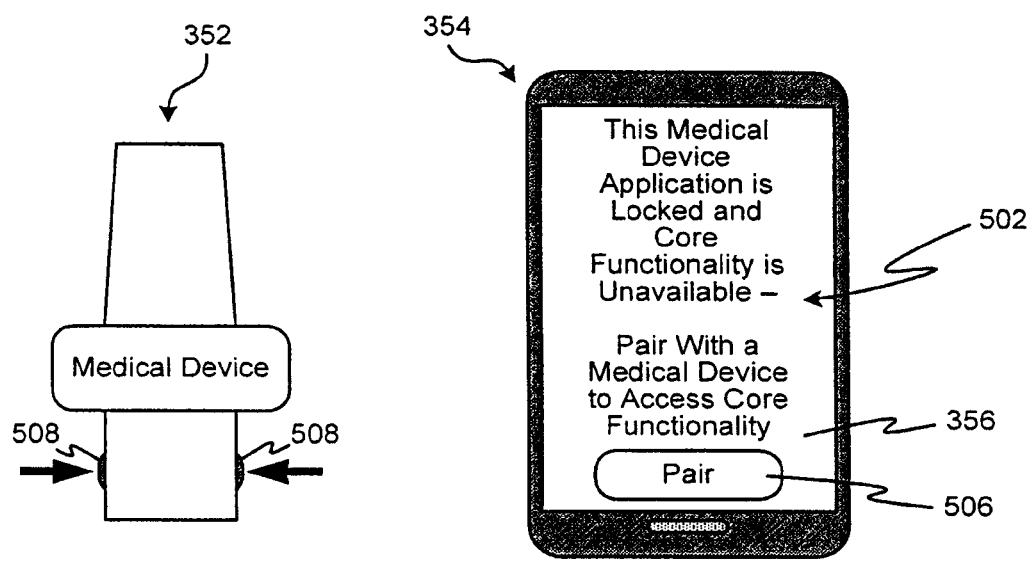
FIGS. 11A-11B show a medical device application shifting from a locked state to an unlocked state, according to one embodiment.
Figure 11B:
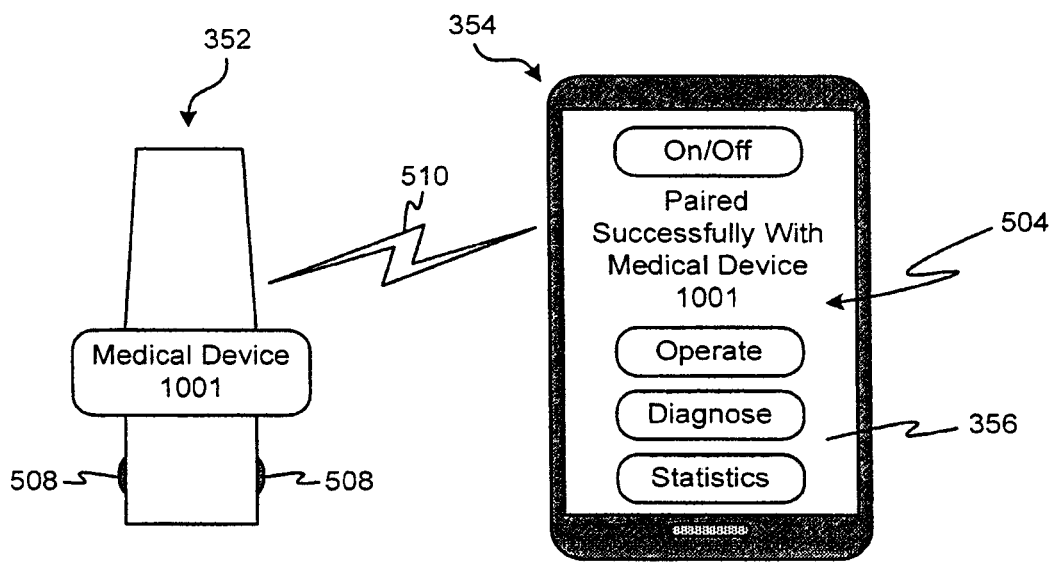

One or more of the following actions may be performed, in various embodiments, to shift the medical device application 356 from the locked state 502 to the unlocked state 504, as shown in FIG. 11. In various embodiments, a triggering event may cause the shifting to occur, such as depression of one or more buttons 508 on the medical device 352, selection of a graphic (such as a visual representation 506 of a button, medical device) on the medical device application 356 (possibly after one or more other factors are verified, such as the identity of the user, medical device type, or proximity of the medical device 352 to the computing device 354), an attempt to utilize the medical device 352 (such as sensing the inhalation of a user through an inhaler). Successful pairing is indicated by the wireless communication line 510 (FIG. 11B).

In another embodiment, in order to unlock the medical device application 356, more than one triggering event may be required. For example, more than one medical device 352 may be in the possession of a user, and unlocking the medical device application 356 may be caused by activation of buttons on both medical devices 352 within a predetermined amount of time, such as 2 seconds, 5 seconds, 10 seconds, 30 seconds, 1 minute, etc. In one example, a first medical device 352 may be an inhaler, such as a nebulizer, while a second medical device 352 may be a medication cartridge that is insertable into the inhaler (nebulizer). In order to unlock the medical device application 356, a user may depress a button on the nebulizer (a first trigger), while also bringing the medication cartridge within wireless sensing range of the computing device 354 (a second trigger), the proximity of the medication cartridge being sensed by the computing device 354.

Once the medical device application 356 is unlocked in this fashion, the identity of the nebulizer and the medication cartridge may be provided to the medical device application 356, thereby allowing for dosage information to be exchanged between the medical device application 356 and the nebulizer, among other useful exchange of information between the two medical devices 352 and the medical device application 356 on the computing device 354. In addition, the unlocking of the medical device application 356 may in turn result in the nebulizer being unlocked and the user being able to take a dose of the medication in the cartridge via the nebulizer. This results in increased security, and additional functionality not available in conventional medical devices and medical device applications.

Figure 12A:
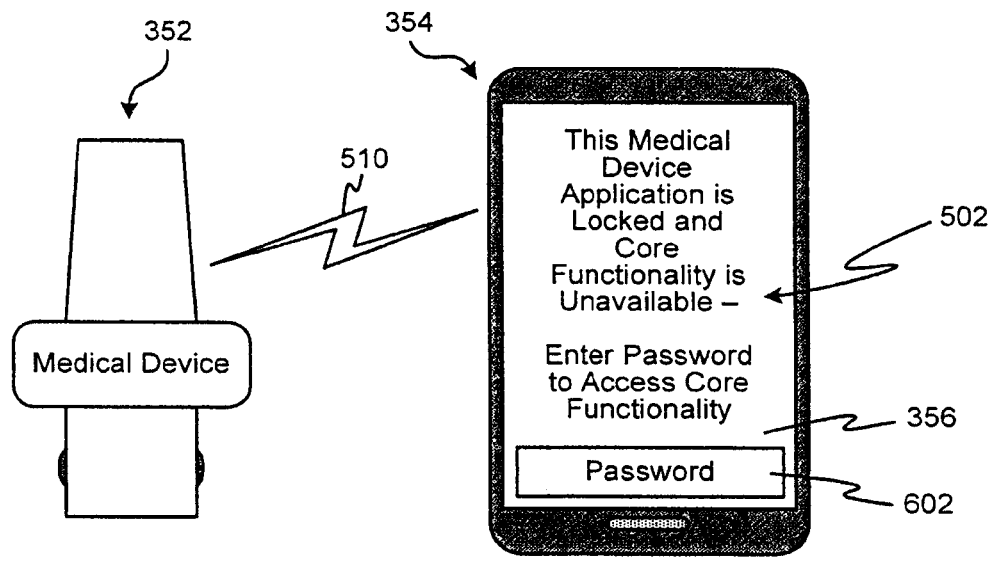
FIGS. 12A-12B show a medical device application shifting from a locked state to an unlocked state, according to another embodiment.
Figure 12B:
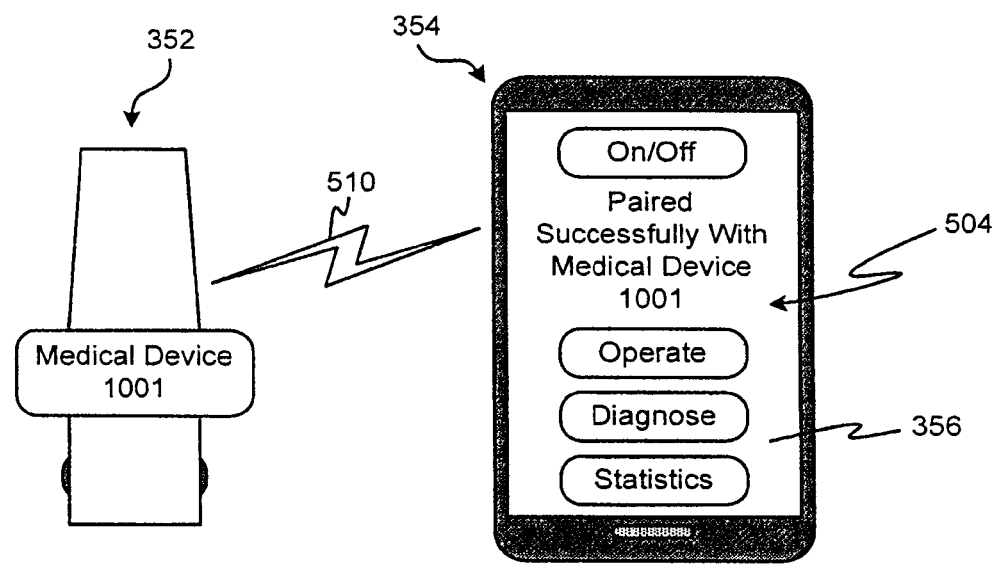

As shown in FIG. 12 in one embodiment, a password may be input into a password field 602 of the medical device application 356 while the medical device 352 is in communication with the medical device application 356 in order to shift the medical device application 356 from the locked state 502 to the unlocked state 504 (FIG. 12B). After this shift, all appropriate functionality of the medical device application 356 becomes accessible to the user, provided that the user's medical device 352 is capable of providing information to the medical device application 356, and is capable of performing actions required by the medical device application 356 to activate the appropriate functionality of the medical device application 356.

In a further embodiment, double security may be provided to the information in the medical device application 356 and to the use of the medical device 352 by requiring that not only must a password be entered in the password field 602 of the medical device application 356, but that the medical device 352 must be in use and in communication with the medical device application 356 in order to shift the medical device application 356 from the locked state 502 to the unlocked state 504.

In another embodiment, the medical device 352 may be physically moved within communication range of the computing device 354 while the medical device application 356 is executing on the computing device 354 and is searching for the medical device 352, using a wireless communication technology, referred to as scanning for an available medical device. Once the medical device 352 is within communication range of the computing device 354, the medical device application 356 may automatically recognize the presence of the medical device 352, shift to the unlocked state, and allow access to all appropriate functionality for the particular medical device 352 within range of the computing device 354.

In this embodiment, the medical device application 356 may still ensure that the user, for which at least some personal information has been entered into the medical device application 356, is intended to be in possession and/or capable of operating the medical device 352 which has caused the medical device application 356 to shift to the unlocked state.

In a further embodiment, should the medical device application 356 determine that the medical device 352 is not intended for use by the user, the medical device application 356 may send an alert to a server (which may be monitored by medical personnel, law enforcement, etc.), shutdown operation of the medical device 352, and/or enter a fault state where another security protocol would need to be overcome in order to access the medical device application 356 again, such as entering of a password, requesting from a provider of the medical device 352 a code and receiving the code to enter into the medical device application 356 to verify the user's identity.

According to another embodiment, a token may be wirelessly passed from the medical device 352 to the medical device application 356 in order to shift the medical device application 356 from the locked state to the unlocked state. After this shift, all appropriate functionality of the medical device application 356 may become accessible to the user, dependent upon which functionality of the medical device application 356 that the user's medical device 352 is capable of utilizing. The token may be specific and unique to at least one of: the user, the medical device 352, a medicament delivered by the medical device 352, the user/medical device combination, etc., and may be recognizable by the medical device application 356 as being indicative of the aforementioned relationship. The token may be a string of numbers, letters, characters, an alphanumeric string, or some other identifying electronic signature capable of being passed wirelessly from the medical device 352 to the medical device application 356.

In another embodiment, a predefined number of communications between the medical device 352 and the medical device application 356 during a predefined time period may be used in order to shift the medical device application 356 from the locked state to the unlocked state. After this shift, all appropriate functionality of the medical device application 356 may become accessible to the user, dependent upon which functionality of the medical device application 356 that the user's medical device 352 is capable of utilizing.

Any number of communications may be used, such as 1, 2, 3, 4, 5, 10, etc., in various embodiments. Furthermore, the predefined time period may vary based on one or more factors, and may be any amount of time, for example 1 to 100 milliseconds, 1 to 10 seconds, or any value therebetween. The factors may include one or more of: a type of the medical device 352, a number of times the medical device application 356 has been accessed, a most recent access of the medical device application 356, the most recent access of the medical device 352, etc.

For example, in some embodiments, three messages sent and received within one second indicating a unique medical device indicator and a unique medical device application indicator may comprise the decision trigger to shift the medical device application 356 from the locked state to the unlocked state. An indicator may be a string of numbers, letters, characters, an alphanumeric string, or some other identifying electronic signature that is difficult to guess and long enough to be unique for all users in a certain geographic location, such as the world, a continent, a country, etc.

In some embodiments, all appropriate functionality of the medical device application 356 may be accessible after the medical device application 356 has been shifted to the unlocked state once during an initial pairing between the medical device 352 and the medical device application 356.

In other embodiments, all appropriate functionality of the medical device application 356 may be accessible as long as the medical device application 356 is maintained in the unlocked state via periodic exchange of messages between the medical device 352 and the medical device application 356 and/or according to random requests for the medical device's unique identifier.

In yet another embodiment, the medical device application 356 may be shifted to the unlocked state each time core functionality is accessed due to a user attempting to access the medical device 352, but not when non-core functionality is attempted to be accessed on the medical device application 356. In this embodiment, the use of non-core functionality on the medical device application 356 will not affect the locked/unlocked state of the medical device application 356. However, attempting to use the medical device 352 will result in the medical device application 356 shifting from the locked to the unlocked state. This embodiment is directed at cases where the medical device 352 has already been verified to be used by an appropriate user, and therefore it's pairing with the medical device application 356 is sufficient to unlock the medical device application 356.

In one embodiment, the medical device application 356 may only be operable with a single medical device 352. Therefore, during a first use of the medical device application 356, information may be provided to the medical device application 356 about the medical device 352, such as by the user, automatically upon the medical device 352 being brought within wireless communication range of the computing device 354, etc. This information about the medical device 352 may be used to ensure that no other medical device is allowed to pair to the particular instance of the medical device application 356 on the computing device 354.

In another embodiment, the medical device application 356 may be operable with more than one medical device 352. In this embodiment, during a first use of each of the medical devices 352, information may be provided to the medical device application 356 about the medical device 352, such as by the user, automatically upon the medical device 352 being brought within wireless communication range of the computing device 354.

In order for the medical device application 356 to remain in the unlocked state, the computing device 352 may monitor via one or more wireless communication channels for predefined information (transmitted from the medical device 352 and received by the computing device 354). The predefined information is captured by the medical device application 356 in an initial pairing, and then the predefined information is listened for, such as in a "heartbeat" function (i.e., a system status) for as long as the medical device application 356 is being accessed by the user.

The heartbeat function may operate by listening for one or more communications, the one or more communications being anticipated to be received according to a predefined schedule, for example, one communication every 10 seconds. When a communication is not received, a proactive message may be sent requesting the communication to ensure that a device is still in communication with another device.

In some embodiments, the continued use of the medical device application 356 triggers a predefined series of communications between the medical device 352 and the medical device application 356 in order to ensure that the medical device 352 remains in the possession of whomever is accessing the medical device application 356, to prevent a single pairing from allowing unfettered access to the medical device application 356 by someone who is not entitled to such access, to protect the private medical information of an authorized user from unauthorized access. The messages that are sent from the medical device 352 to the medical device application 356 may be simple, short packets that indicate the identity of the medical device 352 and the medical device application 356 being accessed. Furthermore, should a predetermined number of messages not be received by the medical device application 356 as anticipated (as arranged between the medical device application 356 and the medical device 352 upon the first pairing), the medical device application 356 may terminate the pairing, stop providing some or all functionality of the medical device application 356 to the user, and/or restrict access to functionality of the medical device 352.

In further embodiments, in addition to the predefined information, the medical device 352 may send payload data to the computing device 354. This payload data may include any useable information that may be gathered, sensed, tracked, created, and/or forwarded by the medical device 352, such as usage data, performance data, energy/battery level and/or battery usage, type of medicament in the medical device 352, remaining medicament level, etc.

Some exemplary payload data that is transmitted from the medical device 352 to the medical device application 356 include total inhalation time for an inhaler, maximum flow rate during inhalation for an inhaler, minimum flow rate during inhalation for an inhaler, total delivered medicament for medicament delivery devices such as needles, inhalers, etc., heart rate for a heart rate monitor, one or more times of activation of the medical device 352, length of medical device 352 activation, among others.

The medical device application 356, upon receiving the signal from the medical device 352, may process the signal to obtain the payload data, and may then define parameters for operation of the medical device application 356. The parameters may include an image to display that matches the medical device 352, a name of the medical device to display, a type of medicament being utilized by the user and stored in the medical device 352, how to interact with the user based on the type of medical device and/or medicament being used, etc. In addition, the medical device application 356, in response to receiving the signal, may compute operating information to display to the user that is relevant to the medical device 352. Operating information may include any useful information to allow the user to utilize the medical device 352.

In various approaches, the operating information may include one or more of the following: a number of doses of medicament to take in a certain period of time (e.g., two doses per day), times for use of the medical device 352 (e.g., check heart rate at 6:00 AM, 12:00 PM, and 6:00 PM), medicament name and drug interaction information (e.g., do not take acetaminophen with alcohol), etc.

In one embodiment, the medical device application 356 may utilize a strength of the signal received from the medical device 352 to determine a proximity of the medical device to the computing device 354. This may be useful for operation within a medical care facility, such as a hospital, nursing home, etc., to enable the computing device 354 to determine which of a plurality of signals is the "right" signal to process, e.g., the closest signal. However, the computing device 354 may cycle through the plurality of signals until the signal that provides the appropriate predefined information is located, and then may lock onto that signal to the exclusion of all others.

The medical device remembers and stores computing devices to which it has been paired previously in an internal memory of the medical device, in one embodiment. The medical device, upon being unpaired, will pair to these computing devices preferentially to any other computing device(s).

The present invention also covers the exact terms, features, values and ranges etc. in case these terms, features, values and ranges etc. are used in conjunction with terms such as about, around, generally, substantially, essentially, at least etc. (i.e., "about 3" shall also cover exactly 3 or "essentially radial" shall also cover exactly radial). The terms "a", "an", "first", "second" etc do not preclude a plurality.

In the claims, the term "comprises/comprising" does not exclude the presence of other elements or steps. Furthermore, although individually listed, a plurality of means, elements or method steps may be implemented. Additionally, although individual features may be included in different claims, these may possibly advantageously be combined, and the inclusion in different claims does not imply that a combination of features is not feasible and/or advantageous. In addition, singular references do not exclude a plurality.

The invention claimed is:

1. An inhaler adapted to supply to a user a formulation carried by a container that comprises a data storage device that includes stored information, an electrically conductive portion, and at least one of an RFID component and a NFC component, the inhaler comprising:
    a) a body adapted to receive the container,
    b) a low-power radio antenna for receiving from the at least one of an RFID component and a NFC component of the container stored information, and
    c) a detector adapted to detect whether the container is opened or pierced,
said detector being adapted to measure an electric characteristic of the container which depends on whether the container is opened or pierced such that said formulation can evacuate said container.

2. An inhaler according to claim 1, wherein the inhaler is adapted to assume an unlocked state and a locked state, the unlocked state allowing the formulation to be supplied to the user and the locked state not allowing the formulation to be supplied to the user.

3. An inhaler according to the claim 2, wherein the inhaler comprises data receiving means adapted to receive data, the inhaler being adapted to change from one state to another in response to data received by the data receiving means.

4. An inhaler according to claim 1, wherein the inhaler is a multi-dose inhaler for supplying formulation comprised in a multi-dose container comprising a plurality of compartments, each of said compartments comprising formulation.

5. A system comprising:
    an inhaler according to claim 1, and
    the container carrying the formulation.

6. A set comprising:
    an inhaler according to claim 1, and
    a computing device external of the inhaler,
    wherein the inhaler and the computing device are adapted to communicate with each other.

7. An inhaler assembly for supplying a formulation to a user, said assembly comprising a container carrying and adapted to supply said formulation and an inhaler having a body adapted to receive said container and allowing the user to selectively move said container with respect to said body, wherein
    said container comprises an electrically conductive portion, a data storage device that includes stored information and data transfer means to transfer said stored information from said container to said inhaler; and
    said inhaler comprises reader means for receiving said stored information from said container, said reader means being carried by said body; and said inhaler further comprises a detector adapted to detect whether said container is opened or pierced, the detector measuring an electric characteristic of said container which depends on whether said container is opened or pierced such that said formulation can evacuate said container.

8. The assembly of claim 7 wherein said data storage device of said container includes at least one of a transponder, a magnetic code, an electronic circuit chip, an optically readable bar code, and a coloring detectable by light.

9. The assembly of claim 8 wherein said inhaler comprises an optoelectronic device to transmit and detect light.

10. The assembly of claim 7 wherein said body defines (1) a container-receiving chamber adapted to restrict movement of said container while therein and (2) a recess that comprises air inlets, the recess being disposed above said container-receiving chamber and sized to allow said container to spin therein.

11. The assembly of claim 10 wherein said inhaler further comprises a mechanism for piercing said container while in said container-receiving chamber.

12. The assembly of claim 7 wherein the inhaler detects movement of the container through its electrically conductive portion and/or data storage means, said container inducing or disrupting a magnetic field and/or an electric field.

13. The inhaler of claim 1 wherein the inhaler comprises an optoelectronic device to transmit and detect light.

14. The inhaler of claim 13 wherein the data storage means comprises a coloring detectable by light.

15. The inhaler of claim 1 further comprising a magnetic field detector and/or an electric field detector and wherein the inhaler is adapted to detect movement of the container.

16. The inhaler of claim 15 wherein movement of the container is detected through its electrically conductive portion and/or data storage means, said container induces a magnetic field and/or disrupts a magnetic and/or an electric field sufficiently to detect movement of the container.

17. The inhaler of claim 1 wherein said body defines (1) a container-receiving chamber adapted to restrict movement of said container while therein and (2) a recess that comprises air inlets, the recess being disposed above said container-receiving chamber and sized to allow said container to spin therein.

18. An inhaler adapted to supply a formulation carried by a container to a user, the container including a data storage device that includes stored information, an electrically conductive portion, and at least one of an RFID component and a NFC component, the inhaler comprising:
    a processor unit adapted to read stored information from the data storage device of the container;
    a detector adapted to detect whether the container or a compartment of the container is opened or pierced, and the detector adapted to measure an electric characteristic of the container, the electric characteristic to be measured by the detector being dependent on whether the container or a respective compartment of the container is opened or pierced.

* * * * *